US010415101B2

(12) United States Patent
Christianson et al.

(10) Patent No.: US 10,415,101 B2
(45) Date of Patent: Sep. 17, 2019

(54) METHODS FOR PRODUCING CANOLA PLANTS WITH CLUBROOT RESISTANCE AND COMPOSITIONS THEREOF

(71) Applicant: Monsanto Technology LLC, St. Louis, MO (US)

(72) Inventors: Jed A. Christianson, Winnipeg (CA); Issa Coulibaly, Saint Peters, MO (US); David O. Niño-Liu, Saint Louis, MO (US); Chunren X. Wu, Winnipeg (CA)

(73) Assignee: Monsanto Technology LLC, St. Louis, MO (US)

( * ) Notice: Subject to any disclaimer, the term of this patent is extended or adjusted under 35 U.S.C. 154(b) by 0 days.

(21) Appl. No.: 15/570,084

(22) PCT Filed: Apr. 27, 2016

(86) PCT No.: PCT/US2016/029613
§ 371 (c)(1),
(2) Date: Oct. 27, 2017

(87) PCT Pub. No.: WO2016/176358
PCT Pub. Date: Nov. 3, 2016

(65) Prior Publication Data
US 2018/0305774 A1    Oct. 25, 2018

Related U.S. Application Data

(60) Provisional application No. 62/155,151, filed on Apr. 30, 2015.

(51) Int. Cl.
| | | |
|---|---|---|
| A01H 5/10 | (2018.01) | |
| C12Q 1/6895 | (2018.01) | |
| A01H 1/04 | (2006.01) | |
| A01H 6/20 | (2018.01) | |

(52) U.S. Cl.
CPC ............. *C12Q 1/6895* (2013.01); *A01H 1/04* (2013.01); *A01H 5/10* (2013.01); *A01H 6/202* (2018.05); *C12Q 2600/13* (2013.01); *C12Q 2600/156* (2013.01); *C12Q 2600/172* (2013.01)

(58) Field of Classification Search
None
See application file for complete search history.

(56) References Cited

U.S. PATENT DOCUMENTS

| | | |
|---|---|---|
| 4,658,085 A | 4/1987 | Beversdorf et al. |
| 5,210,015 A | 5/1993 | Gelfand et al. |
| 5,217,863 A | 6/1993 | Cotton et al. |
| 5,468,613 A | 11/1995 | Erlich et al. |
| 5,563,055 A | 10/1996 | Townsend et al. |
| 5,595,890 A | 1/1997 | Newton et al. |
| 5,616,464 A | 4/1997 | Albagli et al. |
| 5,762,876 A | 6/1998 | Lincoln et al. |
| 5,789,566 A | 8/1998 | Bonhomme et al. |
| 5,800,944 A | 9/1998 | Blonsky et al. |
| 5,876,930 A | 3/1999 | Livak et al. |
| 5,945,283 A | 8/1999 | Kwok et al. |
| 5,973,233 A | 10/1999 | Burns et al. |
| 6,004,744 A | 12/1999 | Goelet et al. |
| 6,013,431 A | 1/2000 | Söderlund et al. |
| 6,030,787 A | 2/2000 | Livak et al. |
| 6,090,558 A | 7/2000 | Butler et al. |
| 6,229,072 B1 | 5/2001 | Burns et al. |
| 6,503,710 B2 | 1/2003 | Gut et al. |
| 6,613,509 B1 | 9/2003 | Chen |
| 6,799,122 B2 | 9/2004 | Benson |
| 6,913,879 B1 | 7/2005 | Schena |
| 6,996,476 B2 | 2/2006 | Najarian |
| 7,135,615 B2 | 11/2006 | Kato |
| 7,238,476 B2 | 7/2007 | McKeown et al. |
| 7,250,252 B2 | 7/2007 | Katz et al. |
| 7,270,981 B2 | 9/2007 | Armes et al. |
| 7,282,355 B2 | 10/2007 | Shi |
| 7,297,485 B2 | 11/2007 | Bornarth et al. |
| 7,312,039 B2 | 12/2007 | Barany et al. |
| 7,935,870 B2 | 5/2011 | Lisieczko et al. |
| 7,947,877 B2 | 5/2011 | Lisieczko |

(Continued)

FOREIGN PATENT DOCUMENTS

| | | |
|---|---|---|
| EP | 0 599 042 | 10/1993 |
| WO | WO 1992/005251 | 4/1992 |

(Continued)

OTHER PUBLICATIONS

*Brassica rapa* subsp. *pekinensis* cultivar Inbred line 'Chiifu' clone KBrB058F21, NCBI/GenBank accession No. AC189404, published Sep. 11, 2008.*
Arends et al., R/qtl: high-throughput Multiple QTL Mapping, *Bioinformatics*, 26:2990-92 (2010).
Bernardo et al., North American Study on Essential Derivation in Maize: Inbreds Developed without and with Selection from F2 Populations, *Theor. Appl. Genet.*, 102:986-992 (2001).
Borevitz et al., Large-Scale Identification of Single-Feature Polymorphisms in Complex Genomes, *Genome Res.*, 13:513-523 (2003).

(Continued)

*Primary Examiner* — Bratislav Stankovic
(74) *Attorney, Agent, or Firm* — Matthew Madsen; Arnold & Porter Kaye Scholer LLP

(57) ABSTRACT

The present disclosure is in the field of plant breeding and disease resistance. The disclosure provides methods for breeding canola plants having clubroot resistance using marker-assisted selection. The disclosure further provides germplasm resistant to various *Plasmodiophora brassicae* pathotypes including pathogtype 5x. The disclosure also provides markers associated with clubroot resistance loci for introgressing these loci into elite germplasm in a breeding program, thus producing novel clubroot resistant germplasm, e.g., spring canola varieties resistant to pathogtype 5x.

20 Claims, 2 Drawing Sheets
Specification includes a Sequence Listing.

(56) References Cited

U.S. PATENT DOCUMENTS

| | | | |
|---|---|---|---|
| 7,964,774 B2 | 6/2011 | Lisieczko |
| 7,982,099 B2 | 7/2011 | Lisieczko |
| 8,071,848 B2 | 12/2011 | Lisieczko |
| 8,138,394 B2 | 3/2012 | Liu et al. |
| 8,143,488 B2 | 3/2012 | Burns et al. |
| 8,148,611 B2 | 4/2012 | Liu et al. |
| 8,153,865 B2 | 4/2012 | Wu et al. |
| 8,507,761 B2 | 8/2013 | Huskowska |
| 8,513,487 B2 | 8/2013 | Lisieczko |
| 8,513,494 B2 | 8/2013 | Wu et al. |
| 8,802,935 B2 | 8/2014 | Huskowska |
| 8,829,282 B2 | 9/2014 | Lisieczko |
| 8,835,720 B2 | 9/2014 | Huskowska |
| 8,851,048 B2 | 10/2014 | Meistrick |
| 8,859,857 B2 | 10/2014 | Burns |
| 8,878,009 B2 | 11/2014 | Wang |
| 2012/0291149 A1 | 11/2014 | Burns |
| 2013/0254929 A1 | 9/2013 | Matsumoto et al. |
| 2013/0298279 A1 | 11/2013 | Gingera et al. |
| 2014/0338012 A1 | 11/2014 | Wu |
| 2014/0338013 A1 | 11/2014 | Burns |
| 2014/0338014 A1 | 11/2014 | Burns |
| 2014/0338015 A1 | 11/2014 | Wu |
| 2014/0338016 A1 | 11/2014 | Wu |

FOREIGN PATENT DOCUMENTS

| | | |
|---|---|---|
| WO | WO 1997/002737 | 1/1997 |
| WO | WO 1998/027806 | 7/1998 |

OTHER PUBLICATIONS

Buczacki et al., Study of Physiologic Specialization in *Plasmidiophora Brassicae*: Proposals for Attempted Rationalization Through an International Approach, *Trans. Br. Mycol. Soc.*, 65:295-303 (1975).

Chalhoub et al., Early Allopolyploid Evolution in the Post-Neolithic *Brassica napus* Oilseed Genome, *Science*, 345(6199):950-53 (2014).

Cruz et al., Characterization of Flowering Time and SSR Marker Analysis of Spring and Winter Type *Brassica napus* L. germplasm, *Euphytica*, 153(1-2):43-57 (2006).

Cui et al., Detecting Single-feature Polymorphisms Using Oligonucleotide Arrays and Robusti, *Bioinformatics*, 21:3852-3858 (2005).

Delourme et al., High-density SNP-based Genetic Map Development and Linkage Disequilibrium Assessment in *Brassica napus* L., *BMC Genomics*, 14:120 (2013).

Diedrichsen et al., Status and Perspectives of Clubroot Resistance Breeding in Crucifer Crops, *J. Plant Growth Regul.*, 28:265-81 (2009).

Flint-Garcia et al., Structure of Linkage Disequilibrium in Plants, *Annu Rev Plant Biol.*, 54:357-374 (2003).

Gaj et al., ZFN, Talen, and CRISPR/Cas-based Methods for Genome Engineering, *Trends in Biotechnology*, 31(7):397-405 (2013).

Hawkins et al., Characterization of Freezing Tolerance and Vernalization in Herewith Vern-a Spring-type *Brassica napus* Line Derived from a Winter Cross, *Planta*, 216:220-26 (2002).

Jannink et al., Association Mapping in Plant Populations, *Quantitative Genetics, Genomics and Plant Breeding*, Kang, Ed. CAB International, pp. 59-68 (2002).

Jansen et al., High Resolution of Quantitative Traits into Multiple Loci via Interval Mapping, *Genetics*, 136:1447-1455 (1994).

Jansen et al., Genotype-by-environment Interaction in Genetic Mapping of Multiple Quantitative Trait Loci, *Theo. Appl. Genet.*, 91:33-37 (1995).

Kosambi, The Estimation of Map Distances from Recombination Values, *Annals of Eugenics*, 12:172-75 (1944).

Kruglyak et al., A Nonparametric Approach for Mapping Quantitative Trait Loci, *Genetics*, 139:1421-1428 (1995).

Lander et al., Mapping Mendelian Factors Underlying Quantitative Traits Using RFLP Linkage Maps, *Genetics*, 121:185-199 (1989).

Liu et al., The *Brassica oleracea* Genome Reveals the Asymmetrical Evolution of Polyploid Genomes, *Nat. Commun.* 5:3930 doi: 10.1038/ncomms4930 (2014).

Openshaw et al., Marker-assisted Selection in Backcross Breeding, in Proceedings of the Symposium "Analysis of Molecular Marker Data," pp. 41-43 (1994).

Pellan-Delourme et al., Cytoplasmic Male Sterility in Rapeseed (*Brassica napus* L.): Female Fertility of Restored Rapeseed with "Ogura" and Cybrids Cytoplasms, *Genome*, 30:234-238 (1988).

Ragot et al., Marker-assisted Backcrossing: A Practical Example, in Techniques *Et Utilisations Des Marqueurs Moleculaires Les Colloques*, 72:45-56 (1995).

Raman et al., A Consensus Map of Rapeseed (*Brassica napus* L.) based on Diversity Array Technology Markers: Applications in Genetic Dissection of Qualitative and Quantitative Traits, *BMC Genomics*, 14:277 (2013).

Reich et al., Linkage Disequilibrium in the Human Genome, *Nature*, 411:199-204 (2001).

Strelkov et al., Characterization of *Plasmodiophora brassicae* Populations from Alberta, Canada, *Can. J. Plant Pathol.*, 28:467-74 (2006).

Wan, et al., Efficient Production of Doubled Haploid Plants Through Colchicine Treatment of Anther-Derived Maize Callus, *Theor. Appl. Genet.*, 77:889-892 (1989).

Wang et al., Integration of Linkage Maps for the Amphidiploid *Brassica napa* and Comparative Mapping with *Arabidopsis* and *Brassica rapa*, *BMC Genomics*, 12:101 (2011).

Wang et al., The Genome of the Mesopolyploid Crop Species *Brassica rapa*, *Nature Genetics*, 43:1035-39 (2011).

Weber, Linkage to Loci for Quantitative Traits (QTLs), *Advances in Plant Breeding*, Blackwell, Berlin, 16 (1994).

Werner et al., Genetic Mapping of Clubroot Resistance Genes in Oilseed Rape, *Theor. Appl Genet*, 116:363-72, at 369, Table 2 (2008).

Williams, A System for the Determination of Races of *Plasmodiophora brassicae* that Infect Cabbage and Rutabaga, *Phytopathology*, 56(6):624-626 (1966).

Yoshikawa, Breeding for Clubroot Resistance of Crucifer Crops in Japan, *Japan Agricultural Research Quarterly*, 17(1):6-11 (1983).

Xu et al., Construction of an Integrated Genetic Linkage Map for the a Genome of *Brassica napus* using SSR Markers Derived from Sequenced BACs in *B. rapa*, *BMC Genomics*, 11:594 (2010).

Xue et al., Isolation and Variation in Virulence of Single-Sport Isolates of *Plasmodiophora brassicae* from Canada, *Plant Dis.*, 92(3):456-462 (2008).

Zeng, Precision Mapping of Quantitative Trait Loci, *Genetics*, 136:1457-1468 (1994).

Chen et al., Identification of Novel QTLs for Isolated-Specific Partial Resistance to *Plasmodiophora brassicae* in *Brassica*, *PLOS One*, 8(12):1-11 (2013).

Cho et al., "Sequence-level comparative analysis of the Brassica napus genome around two stearoyl-ACP desaturase loci," *The Plant Journal* 61(4):591-599 (2010).

Extended European Search Report dated Aug. 18, 2018 in European Application No. EP167870906.

GenBank Accession No. AC189404 *Brassica rapa* subsp. *pekinensis* clone KBrB058F21, complete sequence. Sep. 11, 2008, <https://www.ncbi.nlm.nih.gov/nuccore/AC189404.2> DNA nts 38628-38508.

GenBank Accession No. FP583353 *Brassica napus* var. *napus* clone JBnY117L03 Oct. 31, 2009, <https:www.ncbi.nim.nih.gov/nuccore/262264257> DNA nts 58603-58723.

Li, Zhi-Guo, et al., "Genes encoding the alpha-carboxyltransferase subunit of acetyl-CoA carboxylase from *Brassica napus* and parental species: cloning, expression patterns, and evolution." *Genome* 53(5): 360-370 (2010).

Rahman et al., "Breeding for clubroot resistant spring canola (*Brassica napus* L.) for the Canadian prairies: Can the European winter canola cv. Mendel be used as a source of resistance?" *Can. J. Plant Sci.* 91:447-458 (2011).

(56) References Cited

OTHER PUBLICATIONS

Rahman et al., "Genetics and Breeding for Clubroot Resistance in Canadian spring canola (*Brassica napus* L.)," *Can. J. Plant Pathol.*, 36(S1):122-134 (2014).

* cited by examiner

```
                        SEQUENCE LISTING

<160> NUMBER OF SEQ ID NOS: 56

<210> SEQ ID NO 1
<211> LENGTH: 121
<212> TYPE: DNA
<213> ORGANISM: Glycine max
<220> FEATURE:
<221> NAME/KEY: misc_feature
<222> LOCATION: (61)..(61)
<223> OTHER INFORMATION: n is a, c, g, or t

<400> SEQUENCE: 1
agattttatt gtacttgagc tagaagaaac tgaagaacac cttccawtta ttttatttta      60
nacagcaaaa aagttcaact ggtgaggaaa cgatcagaag ctttgctatg tatatagtat     120
c                                                                    121

<210> SEQ ID NO 2
<211> LENGTH: 121
<212> TYPE: DNA
<213> ORGANISM: Glycine max
<220> FEATURE:
<221> NAME/KEY: misc_feature
<222> LOCATION: (61)..(61)
<223> OTHER INFORMATION: n is a, c, g, or t

<400> SEQUENCE: 2
tttggagcta cttggaagcg aagacatctg tgaactctta gcgtcttcta gtaactttat      60
naacatcytg ttaccacaac ctagggcttc atcyaaagga gtattscccc ayctaattca     120
a                                                                    121

<210> SEQ ID NO 3
<211> LENGTH: 121
<212> TYPE: DNA
<213> ORGANISM: Glycine max
<220> FEATURE:
<221> NAME/KEY: misc_feature
```

<222> LOCATION: (61)..(61)
<223> OTHER INFORMATION: n is a, c, g, or t

<400> SEQUENCE: 3

```
atgatctttc atcaaaatat cggatgagaa agcttgaagc ttcgggactg ctcatatact      60
nttaagkaaa atagtatttg tgtataaaga agtctattag ttagtaaaca aattgagaga     120
a                                                                     121
```

<210> SEQ ID NO 4
<211> LENGTH: 121
<212> TYPE: DNA
<213> ORGANISM: Glycine max
<220> FEATURE:
<221> NAME/KEY: misc_feature
<222> LOCATION: (61)..(61)
<223> OTHER INFORMATION: n is a, c, g, or t

<400> SEQUENCE: 4

```
cttctggttt datacckgtt magmaaatgt catcggtcrg tctgatttga ttgaagaaac      60
nggtaagttg tgcagagact gtgaagctca aggcataggc atagctagca attattcaac    120
c                                                                     121
```

<210> SEQ ID NO 5
<211> LENGTH: 301
<212> TYPE: DNA
<213> ORGANISM: Glycine max
<220> FEATURE:
<221> NAME/KEY: misc_feature
<222> LOCATION: (150)..(150)
<223> OTHER INFORMATION: n is a, c, g, or t

<400> SEQUENCE: 5

```
satcccattt ccagccatag tccggtgggt ttctctggga gttcacttca cagcactgaa      60
actgccatgt cttctctggg atttctctgt aaaatcctgc aaagcccttc aaagtcaaac    120
ctcgtttcca gccatagtca agtggttttn tttgggattt cactacatag cagtgatctt    180
gccacctctc ttgtggatwt tyattaagga agcttccgta ttgtgtttca aaatyggtgt    240
tgtgccttgg atgattggct attggctcga atctgcacc tccccttgt ttggaacgag    300
c                                                                     301
```

<210> SEQ ID NO 6
<211> LENGTH: 121
<212> TYPE: DNA
<213> ORGANISM: Glycine max
<220> FEATURE:
<221> NAME/KEY: misc_feature
<222> LOCATION: (61)..(61)
<223> OTHER INFORMATION: n is a, c, g, or t

<400> SEQUENCE: 6

```
agagattwta attgggatct caaatgatta cacctatagt ttaataagta caattagatg      60
ncaatagctt agcaacacat gattacacat tagtyatcgt ctttcttcta atattaacca    120
c                                                                     121
```

<210> SEQ ID NO 7
<211> LENGTH: 121
<212> TYPE: DNA
<213> ORGANISM: Glycine max
<220> FEATURE:
<221> NAME/KEY: misc_feature
<222> LOCATION: (61)..(61)

<223> OTHER INFORMATION: n is a, c, g, or t

<400> SEQUENCE: 7 ttttatttttg ctaagaaata aatttaccac acatttatct actccatatt atattttta    60 ncgttgttmt agtgcaatwg rattttgacw tgamtaacaa agaacramat sgacgtataa    120
c                                                                    121

<210> SEQ ID NO 8
<211> LENGTH: 121
<212> TYPE: DNA
<213> ORGANISM: Glycine max
<220> FEATURE:
<221> NAME/KEY: misc_feature
<222> LOCATION: (31)..(31)
<223> OTHER INFORMATION: n is a, c, g, or t
<220> FEATURE:
<221> NAME/KEY: misc_feature
<222> LOCATION: (61)..(61)
<223> OTHER INFORMATION: n is a, c, g, or t

<400> SEQUENCE: 8
tatttaggtt cgaattctgg ttactgaaaa nttaacattt cggtatcgtc aaggacatag    60
naccgataca tggtaacaca tgattagtct gaatcacttc tgtaggacta tgatatttt    120 g                                                                    121

<210> SEQ ID NO 9
<211> LENGTH: 276
<212> TYPE: DNA
<213> ORGANISM: Glycine max
<220> FEATURE:
<221> NAME/KEY: misc_feature
<222> LOCATION: (201)..(201)
<223> OTHER INFORMATION: n is a, c, g, or t

<400> SEQUENCE: 9
atcattagtt tggtagagca tatcctataa aaataaaaaa agagaagttt ggtggtgtaa    60
gccaaatatt tgtattatta gccagtaagc tatcaacttc atacccctggt caaatcattg   120 ttcgtattat gaattacttg actcgttaac ttaatttgat taataaacgg aatagtacaa   180
tacatgacgg catccacgac naagtgaaat aacgtgacca agacaaatat caaaagacac   240
gtgttgtgaa cataatggaa gaagcggtcc actaat                              276

<210> SEQ ID NO 10
<211> LENGTH: 279
<212> TYPE: DNA
<213> ORGANISM: Glycine max
<220> FEATURE:
<221> NAME/KEY: misc_feature
<222> LOCATION: (89)..(91)
<223> OTHER INFORMATION: n is a, c, g, or t
<220> FEATURE:
<221> NAME/KEY: misc_feature
<222> LOCATION: (139)..(139)
<223> OTHER INFORMATION: n is a, c, g, or t
<220> FEATURE:
<221> NAME/KEY: misc_feature
<222> LOCATION: (217)..(217)
<223> OTHER INFORMATION: n is a, c, g, or t

<400> SEQUENCE: 10
tctgggtaga cgcttgattt tgggtttcct aaaggactga ttttggagta aagggtcgtc    60 tttttttactc tgtttgtgta gtagtatcnn nttgtgaaca gattcgccgg gattcgtcgg   120
agtatgttca tggtgatgna atgcggcgga gactctgctt tgagttcgta agttcgattc   180

```
tgaacagcaa ctgaactaac gtgttttaat gttttnaaa aagatttctg gtatttgcaa      240
attagacctt aacctctggg taaaatttaa tttaagctt                            279
```

<210> SEQ ID NO 11
<211> LENGTH: 537
<212> TYPE: DNA
<213> ORGANISM: Glycine max
<220> FEATURE:
<221> NAME/KEY: misc_feature
<222> LOCATION: (109)..(109)
<223> OTHER INFORMATION: n is a, c, g, or t
<220> FEATURE:
<221> NAME/KEY: misc_feature
<222> LOCATION: (157)..(157)
<223> OTHER INFORMATION: n is a, c, g, or t
<220> FEATURE:
<221> NAME/KEY: misc_feature
<222> LOCATION: (172)..(172)
<223> OTHER INFORMATION: n is a, c, g, or t
<220> FEATURE:
<221> NAME/KEY: misc_feature
<222> LOCATION: (370)..(370)
<223> OTHER INFORMATION: n is a, c, g, or t

<400> SEQUENCE: 11

```
gcctttgtag ataagattct tatcaaaaag ctgagcaaaa acccaccaaa cactctccat       60
gaacgacaga tccatcgtct tatagtcctt cttgaaatca atccaacgnc cactcctagt     120
gatcaccttc tcccactcct ccacgtagag atccacnacg ctcctacact cntcgttata     180
gttatcaatc cccatctcaa gcacttggga tttcaacttg ataccaaact tcttatcaat    240
caagttctcg atggggaggc catgacagtc ccacccgaag cgacgcgtga cgtggtggcc    300
cgtcatggtc tggtagcgag tcacgatgtc cttgatggtg ccggcgagga tgtggccgta    360
gtgagggagn ccggtggcga aggaggacc gtcgtagaag atgtattcgg ggagatgctc     420
agttcgtctg agctgtgttt tgaaggcatc gatctgagtc cagaaggaga ggactttctc   480
ttcctcgaga ggaaatgaga actccttccc ttcgactact tcttccatgg ctgctgt      537
```

<210> SEQ ID NO 12
<211> LENGTH: 441
<212> TYPE: DNA
<213> ORGANISM: Glycine max
<220> FEATURE:
<221> NAME/KEY: misc_feature
<222> LOCATION: (291)..(291)
<223> OTHER INFORMATION: n is a, c, g, or t

<400> SEQUENCE: 12

```
tagcacgagc ttcacacaat catcagagcc gaagctgtgt gcaaacggat gtggtttctt      60
tggttcgcca tcaaacatgg atctgtgttc gaaatgctac cgagacatat gcgcagagga    120
agctcaaaca gctgttgcaa aagctgccgt tgagaaatct ttcaagccat cgccatcgcc    180
tcctcctcct accctcttca tagcagagcc tgatgtggcg aaaccagaga agaaaaggc    240 ggttgctact gttcttgtgg tggccgagcc atcttctgca acaggagaag ntacagttcc    300
tgaacagaac gaaccaccat ctaaacctgc acggccgaac cggtgccttt gttgcaacaa    360
gaaggttggt atacttgggt ttaagtgcaa atgcgggagc actttctgcg gcgaacatcg    420
gtaccctgag agacatgatt a                                              441
```

<210> SEQ ID NO 13
<211> LENGTH: 27
<212> TYPE: DNA

```
<213> ORGANISM: Glycine max

<400> SEQUENCE: 13
gagctagaag aaactgaaga acacctt                                           27

<210> SEQ ID NO 14
<211> LENGTH: 24
<212> TYPE: DNA
<213> ORGANISM: Glycine max

<400> SEQUENCE: 14
ctgatcgttt cctcaccagt tgaa                                              24

<210> SEQ ID NO 15
<211> LENGTH: 20
<212> TYPE: DNA
<213> ORGANISM: Glycine max

<400> SEQUENCE: 15
cttttttgct gtataaaata                                                   20

<210> SEQ ID NO 16
<211> LENGTH: 16
<212> TYPE: DNA
<213> ORGANISM: Glycine max

<400> SEQUENCE: 16
tttgctgtgt aaaata                                                       16

<210> SEQ ID NO 17
<211> LENGTH: 24
<212> TYPE: DNA
<213> ORGANISM: Glycine max

<400> SEQUENCE: 17
gaagcgaaga catctgtgaa ctct                                              24

<210> SEQ ID NO 18
<211> LENGTH: 22
<212> TYPE: DNA
<213> ORGANISM: Glycine max

<400> SEQUENCE: 18
gaagccctag gttgtggtaa ca                                                22

<210> SEQ ID NO 19
<211> LENGTH: 23
<212> TYPE: DNA
<213> ORGANISM: Glycine max

<400> SEQUENCE: 19
cttctagtaa ctttattaac atc                                               23

<210> SEQ ID NO 20
<211> LENGTH: 21
<212> TYPE: DNA
<213> ORGANISM: Glycine max

<400> SEQUENCE: 20
tctagtaact ttatcaacat c                                                 21

<210> SEQ ID NO 21
<211> LENGTH: 23
```

<212> TYPE: DNA
<213> ORGANISM: Glycine max

<400> SEQUENCE: 21
gatgagaaag cttgaagctt cgg                                             23

<210> SEQ ID NO 22
<211> LENGTH: 36
<212> TYPE: DNA
<213> ORGANISM: Glycine max

<400> SEQUENCE: 22
ttctctcaat ttgtttacta actaatagac ttcttt                               36

<210> SEQ ID NO 23
<211> LENGTH: 21
<212> TYPE: DNA
<213> ORGANISM: Glycine max

<400> SEQUENCE: 23
actgctcata tactattaag t                                               21

<210> SEQ ID NO 24
<211> LENGTH: 20
<212> TYPE: DNA
<213> ORGANISM: Glycine max

<400> SEQUENCE: 24
ctgctcatat actgttaagt                                                 20

<210> SEQ ID NO 25
<211> LENGTH: 23
<212> TYPE: DNA
<213> ORGANISM: Glycine max

<400> SEQUENCE: 25
atcggtcggt ctgatttgat tga                                             23

<210> SEQ ID NO 26
<211> LENGTH: 21
<212> TYPE: DNA
<213> ORGANISM: Glycine max

<400> SEQUENCE: 26
gccttgagct tcacagtctc t                                               21

<210> SEQ ID NO 27
<211> LENGTH: 18
<212> TYPE: DNA
<213> ORGANISM: Glycine max

<400> SEQUENCE: 27
cacaacttac cagtttct                                                   18

<210> SEQ ID NO 28
<211> LENGTH: 17
<212> TYPE: DNA
<213> ORGANISM: Glycine max

<400> SEQUENCE: 28
acaacttacc ggtttct                                                    17

<210> SEQ ID NO 29

```
<211> LENGTH: 23
<212> TYPE: DNA
<213> ORGANISM: Glycine max

<400> SEQUENCE: 29
ctcgtttcca gccatagtca agt                                              23

<210> SEQ ID NO 30
<211> LENGTH: 24
<212> TYPE: DNA
<213> ORGANISM: Glycine max

<400> SEQUENCE: 30
gtggcaagat cactgctatg tagt                                             24

<210> SEQ ID NO 31
<211> LENGTH: 15
<212> TYPE: DNA
<213> ORGANISM: Glycine max

<400> SEQUENCE: 31
atcccaaaga aaacc                                                       15

<210> SEQ ID NO 32
<211> LENGTH: 13
<212> TYPE: DNA
<213> ORGANISM: Glycine max

<400> SEQUENCE: 32
cccaaggaaa acc                                                         13

<210> SEQ ID NO 33
<211> LENGTH: 34
<212> TYPE: DNA
<213> ORGANISM: Glycine max

<400> SEQUENCE: 33
agattttaat tgggatctca aatgattaca ccta                                  34

<210> SEQ ID NO 34
<211> LENGTH: 29
<212> TYPE: DNA
<213> ORGANISM: Glycine max

<400> SEQUENCE: 34
gacgatgact aatgtgtaat catgtgttg                                        29

<210> SEQ ID NO 35
<211> LENGTH: 19
<212> TYPE: DNA
<213> ORGANISM: Glycine max

<400> SEQUENCE: 35
acaattagat gacaatagc                                                   19

<210> SEQ ID NO 36
<211> LENGTH: 17
<212> TYPE: DNA
<213> ORGANISM: Glycine max

<400> SEQUENCE: 36
aattagatgg caatagc                                                     17
```

```
<210> SEQ ID NO 37
<211> LENGTH: 36
<212> TYPE: DNA
<213> ORGANISM: Glycine max

<400> SEQUENCE: 37
gctaagaaat aaatttacca cacatttatc tactcc                              36

<210> SEQ ID NO 38
<211> LENGTH: 25
<212> TYPE: DNA
<213> ORGANISM: Glycine max

<400> SEQUENCE: 38
cgtcgatgtc gttctttgtt agtca                                          25

<210> SEQ ID NO 39
<211> LENGTH: 22
<212> TYPE: DNA
<213> ORGANISM: Glycine max

<400> SEQUENCE: 39
tgcactataa caacgtttaa aa                                             22

<210> SEQ ID NO 40
<211> LENGTH: 20
<212> TYPE: DNA
<213> ORGANISM: Glycine max

<400> SEQUENCE: 40
cactataaca acggttaaaa                                                20

<210> SEQ ID NO 41
<211> LENGTH: 34
<212> TYPE: DNA
<213> ORGANISM: Glycine max

<400> SEQUENCE: 41
tgattaataa acggaatagt acaatacatg acgg                                34

<210> SEQ ID NO 42
<211> LENGTH: 27
<212> TYPE: DNA
<213> ORGANISM: Glycine max

<400> SEQUENCE: 42
cacgtgtctt ttgatatttg tcttggt                                        27

<210> SEQ ID NO 43
<211> LENGTH: 17
<212> TYPE: DNA
<213> ORGANISM: Glycine max

<400> SEQUENCE: 43
catccacgac taagtga                                                   17

<210> SEQ ID NO 44
<211> LENGTH: 15
<212> TYPE: DNA
<213> ORGANISM: Glycine max

<400> SEQUENCE: 44
tccacgacca agtga                                                     15
```

```
<210> SEQ ID NO 45
<211> LENGTH: 21
<212> TYPE: DNA
<213> ORGANISM: Glycine max

<400> SEQUENCE: 45
cgggattcgt cggagtatgt t                                    21

<210> SEQ ID NO 46
<211> LENGTH: 26
<212> TYPE: DNA
<213> ORGANISM: Glycine max

<400> SEQUENCE: 46
agaatcgaac ttacgaactc aaagca                               26

<210> SEQ ID NO 47
<211> LENGTH: 16
<212> TYPE: DNA
<213> ORGANISM: Glycine max

<400> SEQUENCE: 47
catggtgatg gaatgc                                          16

<210> SEQ ID NO 48
<211> LENGTH: 15
<212> TYPE: DNA
<213> ORGANISM: Glycine max

<400> SEQUENCE: 48
atggtgatga aatgc                                           15

<210> SEQ ID NO 49
<211> LENGTH: 27
<212> TYPE: DNA
<213> ORGANISM: Glycine max

<400> SEQUENCE: 49
acagatccat cgtcttatag tccttct                              27

<210> SEQ ID NO 50
<211> LENGTH: 21
<212> TYPE: DNA
<213> ORGANISM: Glycine max

<400> SEQUENCE: 50
aggagtggga gaaggtgatc a                                    21

<210> SEQ ID NO 51
<211> LENGTH: 16
<212> TYPE: DNA
<213> ORGANISM: Glycine max

<400> SEQUENCE: 51
atccaacgcc cactcc                                          16

<210> SEQ ID NO 52
<211> LENGTH: 16
<212> TYPE: DNA
<213> ORGANISM: Glycine max

<400> SEQUENCE: 52
atccaacgac cactcc                                          16
```

```
<210> SEQ ID NO 53
<211> LENGTH: 18
<212> TYPE: DNA
<213> ORGANISM: Glycine max

<400> SEQUENCE: 53
tggccgagcc atcttctg                                                        18

<210> SEQ ID NO 54
<211> LENGTH: 25
<212> TYPE: DNA
<213> ORGANISM: Glycine max

<400> SEQUENCE: 54
cgcatttgca cttaaaccca agtat                                                25

<210> SEQ ID NO 55
<211> LENGTH: 19
<212> TYPE: DNA
<213> ORGANISM: Glycine max

<400> SEQUENCE: 55
aacaggagaa gctacagtt                                                       19

<210> SEQ ID NO 56
<211> LENGTH: 18
<212> TYPE: DNA
<213> ORGANISM: Glycine max

<400> SEQUENCE: 56
acaggagaag gtacagtt                                                        18
```

METHODS FOR PRODUCING CANOLA PLANTS WITH CLUBROOT RESISTANCE AND COMPOSITIONS THEREOF

CROSS-REFERENCE TO RELATED APPLICATIONS

This application is a U.S. National Stage Application of International Application No. PCT/US2016/029613, filed on Apr. 27, 2016, which claims the benefit of U.S. Provisional Application No. 62/155,151, filed on Apr. 30, 2015, which are incorporated by reference in their entireties herein.

FIELD

The present disclosure relates to the field of agricultural biotechnology. More specifically, the disclosure relates to methods for producing canola plants with improved clubroot resistance.

INCORPORATION OF SEQUENCE LISTING

A sequence listing contained in the file named "P34287US01.txt" which is 13,249 bytes (measured in MS-Windows®) and created on Oct. 26, 2017 comprises 56 nucleotide sequences, is filed electronically herewith and incorporated by reference in its entirety.

BACKGROUND

Canola is comprised of three major species that are modified forms (using traditional plant breeding methods) of rapeseed or brown mustard: *Brassica napus* (also known as Argentine canola), *Brassica rapa* (also known as Polish canola), or *Brassica juncea* (canola quality brown mustard). *B. napus*, with its 19 chromosomes, originated from a cross between *B. oleracea* (e.g., cabbage, 9 chromosomes) and *B. rapa* (e.g., turnip, 10 chromosomes). The same is true for *B. juncea*, which originated from a cross between *B. nigra* (e.g., black mustard) and *B. rapa* (e.g., turnip). In the past few years, another mustard species (*Sinapis alba*) has been modified to produce a similar oil profile and meal quality as canola oil. Canola has become increasingly more important to the world, through breeding for better oil quality and improved processing techniques.

Clubroot is a serious soil-borne disease of cruciferous crops. Clubroot is caused by the pathogen *Plasmodiophora brassicae* (*P. brassicae*), which is a protist and an obligate parasite. In canola, it causes swellings or galls to form on the roots and restricts the flow of water and nutrients from roots to aboveground plant tissues. Clubroot also causes stunting through reduced growth, and wilting of leaves is observed under water stress. The disease ultimately causes premature death of the plant. Yield losses due to clubroot are about half of the percentage of infected stems. Severe field infestations by clubroot can cause total yield loss.

Different pathotypes of *P. brassicae* appear to dominate in different canola growing regions. For example, in Canada, pathotypes 3 and 5 were observed in populations from the Alberta region, whereas pathotype 6 was found in populations from British Columbia and Ontario (Strelkov, *Can. J. Plant Pathol.* 28:467-74(2006)). Hildebrand and Delbridge (1995) characterized 10 populations of *P. brassicae* collected from various cruciferous crops in Nova Scotia, and identified eight as pathotype 3, and one each as pathotypes 1 and 2. Similarly, pathotypes 1 and 2 are most prevalent in France while pathotypes 3 and 5 are also found in selected French regions.

Pathotype 5x is a recently discovered pathotype for clubroot. Pathotype 5x is so named because the resistance profile resulting from the usual screening panel of germplasm suggests that it is pathotype 5, but lines resistant to 5 are not resistant to this pathotype. Currently, the origin of pathotype 5x is unclear. It could have originated from genetic breakdown of a previously existing pathotype or could have been a pre-existing, but rare, pathotype. Pathotype 5x has been found to infect all current tolerant canola varieties in Canada. It is predicted that additional novel *P. brassicae* pathotypes or pathotype variants may emerge or be uncovered after more extensive field monitoring and resistance profiling. Strategies for combating clubroot infections by new *P. brassicae* pathotypes are in need.

Currently, there are no economical control measures that can remove the clubroot disease from a canola field once it has been infested. However, it is possible to curtail the spread and reduce the incidence and severity of infection. A number of strategies have been recommended for managing clubroot, including liming of the soil, application of fungicides, use of resistant cultivars, and crop rotation. However, not all of these methods may be practical or affordable. For instance, large amounts of lime may be necessary to increase soil pH sufficiently to reduce disease severity, making this strategy impractical in field crops. Similarly, control of clubroot through the use of fungicides is not always consistent, and may be prohibitively expensive. Crop rotation away from susceptible crops is an effective management strategy, but rotation breaks must be long, as resting spores of the pathogen can survive in the soil for extended periods of time. The use of genetically resistant cultivars is one of the most economically and environmentally desirable strategies for clubroot control.

Several sources of resistance to clubroot have been described within the *Brassica* genus. Some resistances are monogenic, some polygenic, some are dominant, some recessive. Monogenic dominant resistances have been described in *B. rapa* and *B. napus*, such as for example a monogenic dominant resistance in the *B. rapa* Chinese cabbage (Yoshikawa (1983) *Japan Agricultural Research Quarterly*, Vol. 17, no. 1, p. 6-11). Using a resynthesized *B. napus* line (from *B. oleracea* 'Bohmerwaldkohl'× *B. rapa* ECD-04), Werner et al. reported nineteen QTL on chromosomes N02, N03, N08, N13, N15, N16 and N19 giving resistance to seven different clubroot isolates. *Theor Appl Genet*, 116:363-72 (2008). These QTLs were designated as PbBn-Korp-1, PbBn-Korp-2, PbBn-Korp-3, PbBn-Korp-4, PbBn-Korp-5, PbBn-k-1, PbBn-k-2, PbBn-k-3, PbBn-01.07-1, PbBn-01.07-2, PbBn-01.07-3, PbBn-1-1, PbBn-1-2, PbBn-01:60-1, PbBn-01:60-2, PbBn-01:60-3, PbBn-01:60-4, PbBn-e4x04-1, and PbBn-a-1. See Werner et al. *Theor Appl Genet*, 116:363-72, at 369, Table 2 (2008).

Mendel and Tosca, two winter canola varieties, were first introduced to the European seed market in 2000. They both originated in a resynthesized B. *Napus* form and were reported to possess clubroot resistance to specific pathotypes. See Diedrichsen et al., *J Plant Growth Regul*, 28:265-81 (2009). Despite many studies related to the clubroot resistance in Mendel, relatively little is known about the genetic basis of the clubroot resistance in Tosca. Further, transfer of clubroot resistance from winter canola to spring canola could be challenging due to high levels of potential genetic drags associated with the transfer. See Hawkins et al., *Planta* 216:220-26 (2002).

There is a need in canola breeding to identify canola germplasm providing resistance to newly emerging pathotypes (e.g., pathotype 5x) and to develop elite canola varieties that can be grown in regions infected with these new pathotypes. There is also a need to identify resistance loci, haplotypes, and chromosomal intervals that confer or are linked to clubroot resistance, e.g., resistance to pathotype 5x. Additionally, there is a need for a rapid, cost-efficient method to assay, monitor, and introgress clubroot resistance alleles in canola.

SUMMARY

The present disclosure identifies genetic loci conferring clubroot resistance in canola plants, and provides molecular markers linked to these resistance loci. The disclosure further provides methods for introgressing resistance alleles of genetic loci conferring clubroot resistance into plant varieties previously lacking such alleles, thereby providing plants with clubroot resistance. The genetic loci, markers, and methods provided herein therefore allow for production of new varieties with enhanced clubroot resistance.

In some aspects, the disclosure provides a quantitative trait locus (QTL) that demonstrates significant co-segregation with clubroot resistance. The QTL of the disclosure can be tracked during plant breeding or introgressed into a desired genetic background in order to provide novel plants exhibiting enhanced clubroot resistance and one or more other beneficial traits. In particular aspects, the disclosure identifies a QTL interval that is associated with clubroot resistance of canola variety Tosca.

In other aspects, the disclosure provides molecular markers linked to the QTLs disclosed herein and methods of using these markers for detection of and selection for clubroot resistance. Aspects of the disclosure include specific markers and their resistance alleles, chromosome intervals comprising the markers, and methods of detecting markers genetically linked to clubroot resistance to identify plant lines with enhanced clubroot resistance. For example, one aspect of the disclosure provides a chromosome interval associated with clubroot resistance which is flanked by any two of marker loci SEQ ID NOs: 1 to 8 on chromosome N3. Another aspect of the disclosure provides a chromosome interval associated with clubroot resistance, where the interval is flanked by any two of marker loci SEQ ID NOs: 9 to 12 on chromosome N3. Also provided herein are markers, e.g., SEQ ID NOs: 1-12, that are useful for tracking clubroot resistant alleles and can be used in marker assisted selection (MAS) breeding programs to produce plants with enhanced clubroot resistance.

The disclosure further provides methods of using the markers identified herein to introgress loci associated with clubroot resistance into clubroot susceptible plants. Thus, one skilled in the art can use the disclosure to create novel canola plants with clubroot resistance by crossing a donor line comprising a QTL disclosed herein with any desired recipient line, with or without MAS.

This disclosure further provides elite canola spring varieties that are resistant to *P. brassicae* pathotype 5x. Canola plant cells of such varieties are also provided.

BRIEF DESCRIPTION OF THE SEQUENCES

Figure 1:
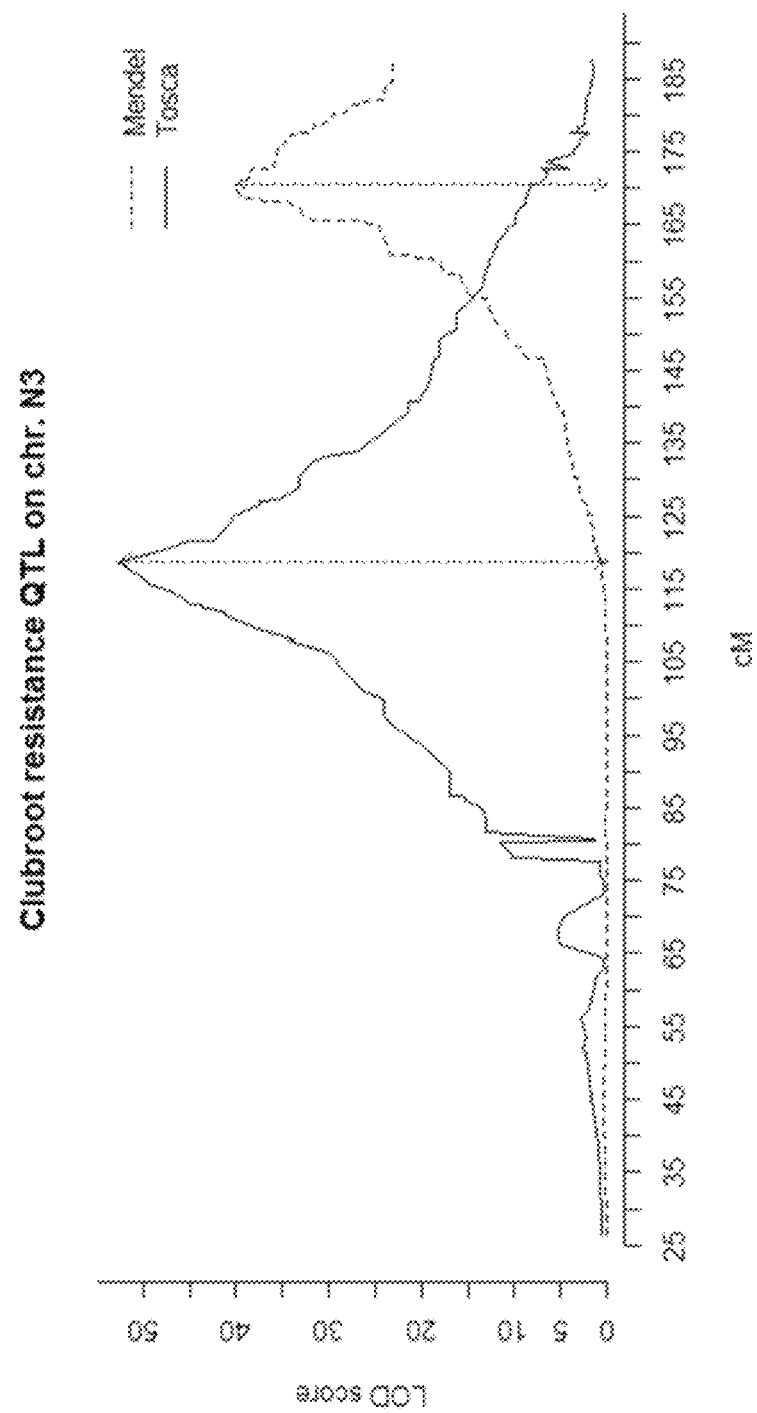
FIG. 1 shows an interval mapping plot of clubroot resistance loci in canola varieties Tosca and Mendel.

SEQ ID NOs: 1 to 8 list sequences of SNP marker loci associated with a clubroot resistance QTL on chromosome N3 (A03) in canola variety Tosca. Example resistant and susceptible alleles of these marker loci are listed in Table 3. SEQ ID NOs: 9-12 list sequences of SNP marker loci associated with a clubroot resistance QTL on chromosome N3 (A03) in canola variety Mendel. SEQ ID NOs: 13-56 list the sequences of primers and probes which can be used to detect the SNP marker loci of SEQ ID NOs: 1-8 and SEQ ID NOs: 9-12.

DETAILED DESCRIPTION

Unless defined otherwise herein, terms are to be understood according to conventional usage by those of ordinary skill in the relevant art. Examples of resources describing many of the terms related to molecular biology used herein can be found in Alberts et al., Molecular Biology of The Cell, 5$^{th}$ Edition, Garland Science Publishing, Inc.: New York, 2007; Rieger et al., Glossary of Genetics: Classical and Molecular, 5th edition, Springer-Verlag: New York, 1991; King et al, A Dictionary of Genetics, 6th ed., Oxford University Press: New York, 2002; and Lewin, Genes IX, Oxford University Press: New York, 2007. The nomenclature for DNA bases as set forth at 37 C.F.R. § 1.822 is used.

As used herein, terms in the singular and the singular forms "a," "an," and "the," for example, include plural referents unless the content clearly dictates otherwise. Thus, for example, reference to "plant," "the plant," or "a plant" also includes a plurality of plants; also, depending on the context, use of the term "plant" can also include genetically similar or identical progeny of that plant; use of the term "a nucleic acid" optionally includes, as a practical matter, many copies of that nucleic acid molecule; similarly, the term "probe" optionally (and typically) encompasses many similar or identical probe molecules.

As used herein, a "canola plant" refers to a plant of species *Brassica napus, B. rapa* (synonymous with *B. campestris*), or *B. juncea* which can be used to produce either the industrial or the edible form of oil.

The *Brassica*-derived industrial form of oil is also called rapeseed oil which has high concentrations of erucic acid, a 22-carbon, single double-bond fatty acid. Rapeseed lines are often referred to as high-erucic acid rapeseed (HEAR) cultivars. Rapeseed oil is used for industrial purposes (e.g., high quality lubricants, hydraulic fluid, slip agents, foam suppressants, surfactants, transmission fluids, cutting fluids, plastics, and high quality polymers). Rapeseed oil can also, however, be used in food processing (e.g., candy bars or as an emulsifier in peanut butter).

Edible canola oil refers to oil that is compliant with the Canadian standard where the oil must contain less than 2 percent erucic acid and where the residual meal contains less than 30 μmoles of total aliphatic glucosinolate per gram of defatted meal. Canola cultivars are often referred to as low erucic acid rapeseed (LEAR) cultivars.

Canola is grown primarily for its seeds which yield between 35% to over 45% oil. After oil is extracted from the seed, the remaining by-product, canola seed meal, is used as a high protein animal feed.

Canola can be roughly grouped into two growth types: winter canola and spring canola. Winter canola is planted in the fall, overwinters, and is harvested the following summer. Winter canola generally requires vernalization to produce flowers. Spring canola is planted in the early spring, requires no vernalization to flower, and is harvested in late summer. Spring and winter lines have evolved for B. napus and B. rapa, while only spring varieties of B. juncea are known. Molecular variations between winter and spring varieties have been reported in B. napus. See Cruz et al., Euphytica, 153(1-2):43-57 (2006).

Different canola types grow in different regions. B. napus winter varieties are grown predominantly in northern Europe, China, and the northwest United States, whereas spring varieties predominate in Canada, northwest China, Denmark, and parts of Sweden. B. rapa has a shorter growing season than B. napus and this trait makes the spring varieties of this species suitable for the more severe climates of Sweden, Finland and Western Canada. B. juncea is grown extensively on the Indian subcontinent.

As used herein, "plant" refers to a whole plant, any part thereof, or a cell or tissue culture derived from a plant, comprising any of: whole plants, plant components or organs (e.g., leaves, stems, roots, etc.), plant tissues, seeds, plant cells, and/or progeny of the same. A progeny plant can be from any filial generation, e.g., $F_1$, $F_2$, $F_3$, $F_4$, $F_5$, $F_6$, $F_7$, etc. A plant cell is a biological cell of a plant, taken from a plant or derived through culture from a cell taken from a plant.

As used herein, "germplasm" refers to living sources of genetic material. The germplasm can be part of an organism or cell, or can be separate from the organism or cell. In general, germplasm provides genetic material with a specific molecular makeup that provides a physical foundation for some or all of the hereditary qualities of an organism or cell culture. As used herein, germplasm includes cells, seed or tissues from which new plants may be grown, or plant parts, such as leaves, stems, pollen, or cells that can be cultured into a whole plant.

As used herein, a "population" of P. brassicae refers to a collection of pathogen resting spores, obtained either from infested soil or from galls of a susceptible plant. Differential pathogenicity or physiological specialization has long been known for P. brassicae and was confirmed in field populations (Williams, Phytopathology, 56(6):624-626 (1966)). Studies have also been performed on the variation in single spore isolates derived from field populations. Since no pathotypes of P. brassicae have been found to be virulent on a single species within a host genus, Buczacki et al., Trans. Br. Mycol. Soc. 65:295-303 (1975) suggested the term "physiologic race" be applied to homogeneous populations of P. brassicae. Others proposed that "pathotype" would be more appropriate, since neither the populations of the pathogen nor the differential hosts possess the genetic uniformity necessary to apply the concept of races to the clubroot pathogen. For the purpose of this application, pathotype is used interchangeably with race or physiologic race.

A population of P. brassicae can be used to inoculate a set of differential hosts to determine its pathotype composition. The differential hosts of Williams (1966) and the European Clubroot Differential (ECD) set (Buczacki et al., 1975) have been used extensively to analyze populations of P brassicae. The pathotype classification based on the differential hosts of Williams (1966) is used here.

Clubroot resistance in canola plants can be evaluated using any known P. brassicae infection assays. For example, canola plants can be inoculated at the time of planting by covering seeds with a layer of cover soil mix containing ground galls. The potted plants are incubated in a growth chamber for approximately 5 to 6 weeks. At the four-leaf stage, the plants are rated for their clubroot resistance. Clubroot infection is rated based on the size and number of galls on the roots (0-3 rating scale; Table 1). A disease index (DI) is then calculated according to the formula:

$$DI = \frac{\sum (0n_0 + 1n_1 + 2n_2 + 3n_3)}{3N} 100$$

with $n_0$ through $n_3$ being the number of plants in each class showing an infection rating of 0 through 3 and N being the total number of plants tested. According to the disease index, plants are rated as either highly resistant (DI<10), resistant (DI between 10 and 20), or moderately-resistant (DI between 20 and 40). Alternatively, plants can also be classified as resistant or susceptible based on visual assessment of root galls.

To test for canola resistance to specific P. brassicae pathogypes, ingle-spore isolates (SSI) are used for plant inoculation. Single-spore isolates have been characterized. See e.g., Xue et al., Plant Disease, 92(3):456-62 (2008). The Chinese cabbage cv. Granaat [European Clubroot Differential (ECD) 05] is generally used as a susceptible check. Generally, three replicates are conducted for each pathotype testing.

As used herein, a "field" comprising spores of P. brassicae refers to a farm field used to grow canola plants and infected with one or more pathotypes of P. brassica.

As used herein, the phrase "associated with" or "linked to" refers to a recognizable and/or assayable relationship between two entities. For example, the phrase "associated with clubroot resistance" refers to a trait, locus, gene, allele, marker, phenotype, etc., or the expression thereof, the presence or absence of which can influence an extent, degree, and/or rate at which a plant or a part of interest thereof that has clubroot resistance. As such, a marker is "associated with" a trait when it is linked to it and when the presence of the marker is an indicator of whether and/or to what extent the desired trait or trait form will occur in a plant/germplasm comprising the marker. Similarly, a marker is "associated with" an allele when it is linked to it and when the presence of the marker is an indicator of whether the allele is present in a plant/germplasm comprising the marker. For example, "a marker associated with clubroot resistance" refers to a marker whose presence or absence can be used to predict whether and to what extent a plant will display a clubroot resistance phenotype.

As used herein, a centimorgan ("cM") is a unit of measure of recombination frequency. One cM is equal to a 1% chance that a marker at one genetic locus will be separated from a marker at a second locus due to crossing over in a single generation.

As used herein, "closely linked" means that the marker or locus is within about 20 cM, 10 cM, 5 cM, 1 cM, 0.5 cM, or less than 0.5 cM of another marker or locus. For example, 20 cM means that recombination between the marker and the locus with a frequency of equal to or less than about 20%.

As used herein, the term "chromosome interval" designates a contiguous linear span of genomic DNA that resides on a single chromosome.

As used herein, "adjacent", when used to describe a nucleic acid molecule that hybridizes to DNA containing a polymorphism, refers to a nucleic acid that hybridizes to DNA sequences that directly abut the polymorphic nucleotide base position. For example, a nucleic acid molecule that can be used in a single base extension assay is "adjacent" to the polymorphism.

As used herein, "locus" is a chromosome region where a polymorphic nucleic acid, trait determinant, gene or marker is located. The loci of this disclosure comprise one or more polymorphisms in a population; e.g., alternative alleles are present in some individuals. A "gene locus" is a specific chromosome location in the genome of a species where a specific gene can be found.

As used herein, "allele" refers to an alternative nucleic acid sequence at a particular locus. The length of an allele can be as small as 1 nucleotide base, but is typically larger. For example, a first allele can occur on one chromosome, while a second allele occurs on a second homologous chromosome, e.g., as occurs for different chromosomes of a heterozygous individual, or between different homozygous or heterozygous individuals in a population.

As used herein, a "resistant allele" is an allele at a particular locus that confers, or contributes to, clubroot resistance, or alternatively, is an allele that allows the identification of plants that comprise clubroot resistance. For example, a resistant marker allele can be a marker allele that segregates with clubroot resistance. A resistant allelic form of a chromosome interval is a chromosome interval that includes a nucleotide sequence that contributes to clubroot resistance at one or more genetic loci physically located in the chromosome interval.

As used herein, "crossed" or "cross" means to produce progeny via fertilization (e.g. cells, seeds or plants) and includes crosses between plants (sexual) and self fertilization (selfing).

As used herein, "backcross" and "backcrossing" refer to the process whereby a progeny plant is repeatedly crossed back to one of its parents. In a backcrossing scheme, the "donor" parent refers to the parental plant with the desired gene or locus to be introgressed. The "recipient" parent (used one or more times) or "recurrent" parent (used two or more times) refers to the parental plant into which the gene or locus is being introgressed. For example, see Ragot, M. et al. Marker-assisted Backcrossing: A Practical Example, in TECHNIQUES ET UTILISATIONS DES MARQUEURS MOLECULAIRES LES COLLOQUES, Vol. 72, pp. 45-56 (1995); and Openshaw et al., Marker-assisted Selection in Backcross Breeding, in PROCEEDINGS OF THE SYMPOSIUM "ANALYSIS OF MOLECULAR MARKER DATA," pp. 41-43 (1994). The initial cross gives rise to the F1 generation. The term "BC1" refers to the second use of the recurrent parent, "BC2" refers to the third use of the recurrent parent, and so on. In some aspects, a backcross is performed repeatedly, with a progeny individual of each successive backcross generation being itself backcrossed to the same parental genotype.

As used herein, "elite line" means any line that has resulted from breeding and selection for superior agronomic performance. Similarly, an "elite germplasm" or elite strain of germplasm is an agronomically superior germplasm. Numerous elite lines are available and known to those of skill in the art of canola breeding, such as GB083 (see U.S. Pat. No. 7,982,099), SCV328921 (see U.S. Pat. No. 7,947,877), SCV425044 (see U.S. Pat. No. 8,829,282), SCV384196 (see U.S. Pat. No. 7,964,774), SCV354718 (see U.S. Pat. No. 7,935,870), SCV218328 (see U.S. Pat. No. 8,071,848), SCV119103 (see U.S. Pat. No. 8,581,048), SCV431158 (see U.S. Pat. No. 8,138,394), SCV453784 (see U.S. Pat. No. 8,148,611), SCV470336 (see U.S. Pat. No. 8,143,488), SCV152154 (see U.S. Pat. No. 8,153,865), ND-662c (see U.S. Pat. No. 8,513,487), SCV291489 (see U.S. Publication 20120291149), SCV695971 (see U.S. Pat. No. 8,513,494), SCV372145 (see U.S. Pat. No. 8,507,761), SCV259778 (see U.S. Pat. No. 8,859,857), SCV318181 (see U.S. Pat. No. 8,878,009), SCV942568 (see U.S. Pat. No. 8,802,935), SCV967592 (see U.S. Pat. No. 8,835,720), SCV816796 (see U.S. Publication 20140338012), SCV435009 (see U.S. Publication 20140338014), SCV366592 (see U.S. Publication 20140338013), SCV569538 (see U.S. Publication 20140338015), and SCV822805 (see U.S. Publication 20140338016).

As used herein, "genetic element" or "gene" refers to a heritable sequence of DNA, e.g., a genomic sequence, with functional significance. The term "gene" can also be used to refer to, e.g., a cDNA and/or an mRNA encoded by a genomic sequence, as well as to that genomic sequence.

As used herein, "genotype" is the genetic constitution of an individual (or group of individuals) at one or more genetic loci, as contrasted with the observable trait (phenotype). Genotype is defined by the allele(s) of one or more known loci that the individual has inherited from its parents. The term genotype can be used to refer to an individual's genetic constitution at a single locus, at multiple loci, or, more generally, the term genotype can be used to refer to an individual's genetic make-up for all the genes in its genome.

As used herein, a "haplotype" is the genotype of an individual at a plurality of genetic loci. Typically, the genetic loci described by a haplotype are physically and genetically linked, e.g., in the same chromosome interval. Selection based upon a haplotype can be more effective than selection based upon a single marker locus.

As used herein, "selecting" or "selection" in the context of marker-assisted selection or breeding refer to the act of picking or choosing desired individuals, normally from a population, based on certain pre-determined criteria.

As used herein, the terms "phenotype," or "phenotypic trait" or "trait" refers to one or more detectable characteristics of a cell or organism which can be influenced by genotype. The phenotype can be observable to the naked eye, or by any other means of evaluation known in the art, e.g., microscopy, biochemical analysis, genomic analysis, an assay for a particular disease tolerance, etc. In some cases, a phenotype is directly controlled by a single gene or genetic locus, e.g., a "single gene trait." In other cases, a phenotype is the result of several genes.

As used herein, "linkage disequilibrium" (LD) refers to a non-random segregation of genetic loci or traits (or both). In either case, linkage disequilibrium implies that the relevant loci are within sufficient physical proximity along a length of a chromosome so that they segregate together with greater than random (i.e., non-random) frequency (in the case of co-segregating traits, the loci that underlie the traits are in sufficient proximity to each other). Linked loci cosegregate more than 50% of the time, e.g., from about 51% to about 100% of the time. Linkage disequilibrium can be measured using any one of the methods provided in Hedrick, Gametic disequilibrium measures: proceed with caution. *Genetics*, 117:331-41 (1987). The term "physically linked" is sometimes used to indicate that two loci, e.g., two marker loci, are physically present on the same chromosome. Advantageously, the two linked loci are located in close proximity such that recombination between homologous chromosome pairs does not occur between the two loci during meiosis with high frequency, e.g., such that linked loci cosegregate at least about 90% of the time, e.g., 91%, 92%, 93%, 94%, 95%, 96%, 97%, 98%, 99%, 99.5%, 99.75%, or more of the time.

As used herein, "marker assay" means a method for detecting a polymorphism at a particular locus using a particular method, e.g., measurement of at least one phenotype (such as seed color, flower color, or other visually detectable trait), restriction fragment length polymorphism (RFLP), single base extension, electrophoresis, sequence alignment, allelic specific oligonucleotide hybridization (ASO), random amplified polymorphic DNA (RAPD), microarray-based technologies, and nucleic acid sequencing technologies, etc.

As used herein, "marker assisted selection" (MAS) is a process by which phenotypes are selected based on marker genotypes. "Marker assisted selection breeding" refers to the process of selecting a desired trait or traits in a plant or plants by detecting one or more nucleic acids from the plant, where the nucleic acid is linked to the desired trait, and then selecting the plant or germplasm possessing those one or more nucleic acids.

As used herein, "polymorphism" means the presence of one or more variations in a population. A polymorphism may manifest as a variation in the nucleotide sequence of a nucleic acid or as a variation in the amino acid sequence of a protein. Polymorphisms include the presence of one or more variations of a nucleic acid sequence or nucleic acid feature at one or more loci in a population of one or more individuals. The variation may comprise but is not limited to one or more nucleotide base changes, the insertion of one or more nucleotides or the deletion of one or more nucleotides. A polymorphism may arise from random processes in nucleic acid replication, through mutagenesis, as a result of mobile genomic elements, from copy number variation and during the process of meiosis, such as unequal crossing over, genome duplication and chromosome breaks and fusions. The variation can be commonly found or may exist at low frequency within a population, the former having greater utility in general plant breeding and the latter may be associated with rare but important phenotypic variation. Useful polymorphisms may include single nucleotide polymorphisms (SNPs), insertions or deletions in DNA sequence (Indels), simple sequence repeats of DNA sequence (SSRs), a restriction fragment length polymorphism, and a tag SNP. A genetic marker, a gene, a DNA-derived sequence, a RNA-derived sequence, a promoter, a 5' untranslated region of a gene, a 3' untranslated region of a gene, microRNA, siRNA, a tolerance locus, a satellite marker, a transgene, mRNA, ds mRNA, a transcriptional profile, and a methylation pattern may also comprise polymorphisms. In addition, the presence, absence, or variation in copy number of the preceding may comprise polymorphisms.

As used herein, "SNP" or "single nucleotide polymorphism" means a sequence variation that occurs when a single nucleotide (A, T, C, or G) in the genome sequence is altered or variable. "SNP markers" exist when SNPs are mapped to sites on the genome.

As used herein, "marker" or "molecular marker" or "marker locus" is a term used to denote a nucleic acid or amino acid sequence that is sufficiently unique to characterize a specific locus on the genome. Any detectable polymorphic trait can be used as a marker so long as it is inherited differentially and exhibits linkage disequilibrium with a phenotypic trait of interest. A number of markers and integrated genetic maps have been developed for various canola species. See Xu et al. *BMC Genomics* 2010, 11:594; Wang et al. *BMC Genomics* 2011, 12:101; Raman et al. *BMC Genomics* 2013, 14:277; Delourme et al. *BMC Genomics* 2013, 14:120. All markers are used to define a specific locus in canola genomes. Large numbers of these markers have been mapped. Each marker is therefore an indicator of a specific segment of DNA, having a unique nucleotide sequence. The map positions provide a measure of the relative positions of particular markers with respect to one another. When a trait is stated to be linked to a given marker it will be understood that the actual DNA segment whose sequence affects the trait generally co-segregates with the marker. More precise and definite localization of a trait can be obtained if markers are identified on both sides of the trait. By measuring the appearance of the marker(s) in progeny of crosses, the existence of the trait can be detected by relatively simple molecular tests without actually evaluating the appearance of the trait itself, which can be difficult and time-consuming because the actual evaluation of the trait requires growing plants to a stage and/or under environmental conditions where the trait can be expressed. Molecular markers have been widely used to determine genetic composition in canola. Additional markers can also be designed and tested based on the available genome sequences of various canola species. See e.g., Chalhoub et al., "Early allopolyploid evolution in the post-Neolithic *Brassica napus* oilseed genome," *Science* 345(6199):950-53 (2014); Liu et al., "The *Brassica oleracea* genome reveals the asymmetrical evolution of polyploid genomes," *Nat. Commun.* 5:3930 doi: 10.1038/ncomms4930 (2014); Wang et al., "The genome of the mesopolyploid crop species *Brassica rapa*," *Nature Genetics* 43:1035-39 (2011). In some aspects, markers used herein exhibit LOD scores of 2 or greater, 3 or greater, 4 or greater, 5 or greater, 6 or greater, 7 or greater, 8 or greater, or 9 or greater with clubroot resistance loci disclosed herein, measuring using a method known in the art such as Qgene Version 2.23 (1996) and default parameters.

As used herein, a "genetic recombination frequency" is the frequency of a crossing over event (recombination) between two genetic loci. Recombination frequency can be observed by following the segregation of markers and/or traits following meiosis. In some cases, two different markers can have the same genetic map coordinates. In that case, the two markers are in such close proximity to each other that recombination occurs between them with such low frequency that it is undetected.

As used herein, "mapping" is the process of defining the linkage relationships of loci through the use of genetic markers, populations segregating for the markers, and standard genetic principles of recombination frequency.

As used herein, a "genetic map" is the relationship of genetic linkage among loci on one or more chromosomes (or linkage groups) within a given species, generally depicted in a diagrammatic or tabular form. "Genetic mapping" is the process of defining the linkage relationships of loci through the use of genetic markers, populations segregating for the markers, and standard genetic principles of recombination frequency. A "genetic map location" is a location on a genetic map relative to surrounding genetic markers on the same linkage group where a specified marker can be found within a given species. In contrast, a "physical map" of the genome refers to absolute distances (for example, measured in base pairs or isolated and overlapping contiguous genetic fragments, e.g., contigs). In general, the closer two markers or genomic loci are on the genetic map, the closer they lie to one another on the physical map. A physical map of the genome does not take into account the genetic behavior (e.g., recombination frequencies) between different points on the physical map. A lack of precise proportionality between genetic distances and physical distances can exist due to the fact that the likelihood of genetic recombination is not uniform throughout the genome; some chromosome regions are cross-over "hot spots," while other regions demonstrate only rare recombination events, if any. Genetic mapping variability can also be observed between different populations of the same crop species. In spite of this variability in the genetic map that may occur between populations, genetic map and marker information derived from one population generally remains useful across multiple populations in identification of plants with desired traits, counter-selection of plants with undesirable traits and in MAS breeding. As one of skill in the art will recognize, recombination frequencies (and as a result, genetic map positions) in any particular population are not static. The genetic distances separating two markers (or a marker and a QTL) can vary depending on how the map positions are determined. For example, variables such as the parental mapping populations used, the software used in the marker mapping or QTL mapping, and the parameters input by the user of the mapping software can contribute to the QTL marker genetic map relationships. However, it is not intended that the disclosure be limited to any particular mapping populations, use of any particular software, or any particular set of software parameters to determine linkage of a particular marker or chromosome interval with a desired phenotype. It is well within the ability of one of ordinary skill in the art to extrapolate the novel features described herein to any gene pool or population of interest, and using any particular software and software parameters. Indeed, observations regarding genetic markers and chromosome intervals in populations in addition to those described herein are readily made using the teaching of the present disclosure. In some aspects, genetic distances referred herein are calculated from recombination values using the Kosambi function (Kosambi, The estimation of map distances from recombination values. *Annals of Eugenics,* 12:172-75 (1944)).

As used herein, "primer" refers to an oligonucleotide (synthetic or occurring naturally), which is capable of acting as a point of initiation of nucleic acid synthesis or replication along a complementary strand when placed under conditions in which synthesis of a complementary strand is catalyzed by a polymerase. Typically, primers are about 10 to 30 nucleotides in length, but longer or shorter sequences can be employed. Primers may be provided in double-stranded form, though the single-stranded form is more typically used. A primer can further contain a detectable label, for example a 5' end label.

As used herein, "probe" refers to an oligonucleotide (synthetic or occurring naturally) that is complementary (though not necessarily fully complementary) to a polynucleotide of interest and forms a duplex structure by hybridization with at least one strand of the polynucleotide of interest. Typically, probes are oligonucleotides from 10 to 50 nucleotides in length, but longer or shorter sequences can be employed. A probe can further contain a detectable label.

As used herein, a "population of plants" or "plant population" means a set comprising any number, including one, of individuals, objects, or data from which samples are taken for evaluation. Most commonly, the terms relate to a breeding population of plants from which members are selected and crossed to produce progeny in a breeding program. A population of plants can include the progeny of a single breeding cross or a plurality of breeding crosses, and can be either actual plants or plant derived material, or in silico representations of the plants. The population members need not be identical to the population members selected for use in subsequent cycles of analyses or those ultimately selected to obtain final progeny plants. Often, a plant population is derived from a single biparental cross, but may also derive from two or more crosses between the same or different parents. Although a population of plants may comprise any number of individuals, those of skill in the art will recognize that plant breeders commonly use population sizes ranging from one or two hundred individuals to several thousand, and that the highest performing 5-20% of a population is what is commonly selected to be used in subsequent crosses in order to improve the performance of subsequent generations of the population.

As used herein, "cultivar" and "variety" are used synonymously and mean a group of plants within a species (e.g., *B. napus*) that share certain genetic traits that separate them from other possible varieties within that species. Canola cultivars can be inbreds or hybrids, though commercial canola cultivars are mostly hybrids to take advantage of hybrid vigor. Individuals within a canola hybrid cultivar are homogeneous, nearly genetically identical, with most loci in the heterozygous state.

As used herein, "resistance" and "enhanced resistance" are used interchangeably herein and refer to any type of increase in resistance, or any type of decrease in susceptibility. A "resistant plant" or "resistant plant variety" need not possess absolute or complete resistance. Instead, a "resistant plant," "resistant plant variety," or a plant or plant variety with "enhanced resistance" will have a level of resistance which is higher than that of a comparable susceptible plant or variety. The level of clubroot resistance can be determined based on disease indexes as calculated in Example 1.

As used herein, "introgression" refers to the transmission of a desired allele of a genetic locus from one genetic background to another.

As used herein, "quantitative trait locus (QTL)" or "quantitative trait loci" (QTLs) refer to a genetic domain that effects a phenotype that can be described in quantitative terms and can be assigned a "phenotypic value" which corresponds to a quantitative value for the phenotypic trait.

As used herein, "oil content" is measured as a percent of the whole dried seed and is variety-specific. It can be determined using various analytical techniques such as nuclear magnetic resonance (NMR) spectroscopy, near-infrared (NIR) spectroscopy, and Soxhlet extraction.

As used herein, "single gene converted" or "single gene conversion" refers to plants that are developed using a plant breeding technique known as backcrossing, or via genetic engineering, wherein essentially all of the desired morphological and physiological characteristics of a variety are recovered in addition to the single gene transferred into the variety via the backcrossing technique or via genetic engineering.

In one aspect, this disclosure provides methods of selecting a canola plant with clubroot resistance. These methods comprise: (a) detecting in a population of canola plants a canola plant comprising a clubroot resistant allele at a polymorphic locus within 20 cM of any one of marker loci SEQ ID NOs: 1-8; and (b) selecting the canola plant comprising the clubroot resistant allele. In some aspects, these methods comprise detecting a clubroot resistant allele at a polymorphic locus within about 15 cM, 10 cM, 5 cM, 1 cM, 0.5 cM, or less than 0.5 cM of any one of marker loci SEQ ID NOs: 1-8. In other aspects, these methods comprise detecting a clubroot resistant allele at at least one polymorphic locus selected from the group consisting of SEQ ID NOs: 1-8. In some aspects, these methods are used to select a *B. napus* or *B. rapa* plant. In some aspects, these methods are used to select a plant from the group consisting of rutabaga, oil rape, Chinese cabbage, pak Choi, and turnip. In other aspects, these methods are used to select a winter canola variety or a spring canola variety. In a further aspect, these methods are used to select a winter canola variety. In some aspects, these methods are used to select canola plants highly resistant, resistant, or moderately resistant to at least one *P. brassicae* pathotype selected from the group consisting of pathotypes 1 to 9, G, H, and 5x. In other aspects, canola plants selected by these methods are highly resistant, resistant, or moderately resistant to at least one *P. brassicae* pathotype selected from the group consisting of pathotypes 2, 3, 5, 5x, 6, 8, and G. In some aspects, these methods comprise using a marker assay, detecting a haplotype, assaying a SNP marker, or the use of an oligonucleotide probe. In other aspects, oligonucleotide probes used in these methods are adjacent to a polymorphic nucleotide position in the polymorphic locus.

In another aspect, this disclosure provides methods of selecting a canola plant with clubroot resistance, which methods comprise (a) providing a population of canola plants; (b) detecting in the population a canola plant comprising a clubroot resistant allele at a polymorphic locus within 20 cM, 15 cM, 10 cM, 5 cM, 1 cM, 0.5 cM, or less than 0.5 cM of any one of marker loci SEQ ID NOs: 1-8; and (c) selecting the canola plant comprising the clubroot resistant allele.

In another aspect, this disclosure provides methods of producing a canola plant with enhanced clubroot resistance. These methods comprise (a) crossing a first canola plant comprising a clubroot resistant allele with a second canola plant of a different genotype to produce one or more progeny plants; and (b) selecting a progeny plant comprising the clubroot resistant allele, wherein the clubroot resistant allele is in a chromosomal segment flanked by any two of marker loci SEQ ID NOs: 1 to 8 on chromosome N3. In some aspects, these methods comprise detecting a clubroot resistant allele at a polymorphic locus within about 4 cM, 1 cM, 0.5 cM, or less than 0.5 cM of any one of marker loci SEQ ID NOs: 1-8. In other aspects, these methods comprise detecting a clubroot resistant allele at at least one polymorphic locus selected from the group consisting of SEQ ID NOs: 1-8. In some aspects, these methods further comprise (c) developing a doubled haploid plant from a microspore of the selected progeny plant. In other aspects, these methods further comprise (d) backcrossing the doubled haploid plant with the second canola plant. In some aspects, these methods further comprise (c) crossing the selected progeny plant with itself or the second plant to produce one or more further progeny plants; and (d) selecting a further progeny plant comprising the clubroot resistant allele. In some aspects, step (c) comprises backcrossing. In other aspects, step (c) comprises 2 to 7 generations of backcrosses. In some aspects, step (d) comprises marker-assisted selection. In some aspects, these methods are used to produce a *B. napus* or *B. rapa* plant. In some aspects, these methods are used to select a plant from the group consisting of rutabaga, oil rape, Chinese cabbage, pak choi, and turnip. In some aspects, these methods are used to produce an inbred or a hybrid. In other aspects, these methods are used to produce a winter canola variety or a spring canola variety. In a further aspect, these methods are used to produce a winter canola variety. In some aspects, these methods are used to produce canola plants highly resistant, resistant, or moderately resistant to at least one *P. brassicae* pathotype selected from the group consisting of pathotypes 1 to 9, G, H, and 5x. In other aspects, canola plants produced by these methods are highly resistant, resistant, or moderately resistant to at least one *P. brassicae* pathotype selected from the group consisting of pathotypes 2, 3, 5, 5x, 6, 8, and G. In some aspects, these methods comprise using a marker assay, detecting a haplotype, assaying a SNP marker, or the use of an oligonucleotide probe. In other aspects, oligonucleotide probes used in these methods are adjacent to a polymorphic nucleotide position in the polymorphic locus.

In a further aspect, this disclosure provides methods for creating a population of canola plants with clubroot resistance, which methods comprise: (a) genotyping a first population of canola plants for a marker closely linked to a first clubroot resistance locus and for a marker closely linked to a second clubroot resistance locus, wherein the first clubroot resistance locus located in a chromosomal segment flanked by any two of marker loci SEQ ID NOs: 1 to 8 on chromosome N3; (b) selecting from the first population one or more canola plants containing the first and second clubroot resistance loci; (c) producing a population of offspring from the selected one or more canola plants. In some aspects, these methods comprise selection of a second clubroot resistance locus selected from the group consisting of Crr1, Crr2, Crr3, Crr4, CRa, CRb, CRc, CRk. See Diederichsen et al., *J. Plant Growth Regul* (2009) 28:265-81. In other aspects, these methods comprise selection of a second clubroot resistance locus selected from the group consisting of PbBn-Korp-1, PbBn-Korp-2, PbBn-Korp-3, PbBn-Korp-4, PbBn-Korp-5, PbBn-k-1, PbBn-k-2, PbBn-k-3, PbBn-01.07-1, PbBn-01.07-2, PbBn-01.07-3, PbBn-1-1, PbBn-1-2, PbBn-01:60-1, PbBn-01:60-2, PbBn-01:60-3, PbBn-01:60-4, PbBn-e4x04-1, and PbBn-a-1. See Werner et al. *Theor Appl Genet,* 116:363-72, at 369, Table 2 (2008). In further aspects, the second clubroot resistance locus selected by the methods disclosed herein is a clubroot resistance locus present on chromosome N3 in canola variety Mendel. In further aspects, the second clubroot resistance locus is located in a chromosomal segment flanked by any two of marker loci SEQ ID NOs: 9 to 12. In further aspects, the second clubroot resistance locus is within about 20 cM, 10 cM, 5 cM, 4 cM, 3 cM, 2 cM, 1 cM, 0.5 cM, or less than 0.5 cM of any one of marker loci SEQ ID NOs: 9 to 12.

In some aspects, selection of the Mendel-derived clubroot resistance QTL is carried out by genotyping and selection of a polymorphic locus between 168 cM and 172 cM, between 165 cM and 175 cM, between 160 cM and 180 cM, between 155 cM and 185 cM, or between 150 cM and 190 cM on chromosome N3. In other aspects, selection of the Mendel-derived clubroot resistance QTL is carried out by genotyping and selection of a marker linked to, associated with, or with about 20 cM, 10 cM, 5 cM, 1 cM, 0.5 cM, or less than 0.5 cM of any one of marker loci SEQ ID NOs: 9-12.

In one aspect, this disclosure provides methods of selecting a canola plant with clubroot resistance. These methods comprise (a) detecting in a population of canola plants a canola plant comprising a clubroot resistant allele at a polymorphic locus within 20 cM of any one of marker loci SEQ ID NOs: 9-12; and (b) selecting the canola plant comprising the clubroot resistant allele. In some aspects, these methods comprise detecting a clubroot resistant allele at a polymorphic locus within about 15 cM, 10 cM, 5 cM, 1 cM, 0.5 cM, or less than 0.5 cM of any one of marker loci SEQ ID NOs: 9-12. In other aspects, these methods comprise detecting a clubroot resistant allele at at least one polymorphic locus selected from the group consisting of SEQ ID NOs: 9-12. In some aspects, these methods are used to select a *B. napus* or *B. rapa* plant. In some aspects, these methods are used to select a plant from the group consisting of rutabaga, oil rape, Chinese cabbage, pak Choi, and turnip. In other aspects, these methods are used to select a winter canola variety or a spring canola variety. In a further aspect, these methods are used to select a winter canola variety. In some aspects, these methods are used to select canola plants highly resistant, resistant, or moderately resistant to at least one *P. brassicae* pathotype selected from the group consisting of pathotypes 1 to 9, G, H, and 5x. In other aspects, canola plants selected by these methods are highly resistant, resistant, or moderately resistant to at least one *P. brassicae* pathotype selected from the group consisting of pathotypes 2, 3, 5, 5x, 6, 8, and G. In some aspects, these methods comprise using a marker assay, detecting a haplotype, assaying a SNP marker, or the use of an oligonucleotide probe. In other aspects, oligonucleotide probes used in these methods are adjacent to a polymorphic nucleotide position in the polymorphic locus.

In another aspect, this disclosure provides methods of producing a canola plant with enhanced clubroot resistance. These methods comprise (a) crossing a first canola plant comprising a clubroot resistant allele with a second canola plant of a different genotype to produce one or more progeny plants; and (b) selecting a progeny plant comprising the clubroot resistant allele, wherein the clubroot resistant allele is in a chromosomal segment flanked by any two of marker loci SEQ ID NOs: 9-12 on chromosome N3. In some aspects, these methods comprise detecting a clubroot resistant allele at a polymorphic locus within about 4 cM, 1 cM, 0.5 cM, or less than 0.5 cM of any one of marker loci SEQ ID NOs: 9-12. In other aspects, these methods comprise detecting a clubroot resistant allele at at least one polymorphic locus selected from the group consisting of SEQ ID NOs: 9-12. In some aspects, these methods further comprise (c) developing a doubled haploid plant from a microspore of the selected progeny plant. In other aspects, these methods further comprise (d) backcrossing the doubled haploid plant with the second canola plant. In some aspects, these methods further comprise (c) crossing the selected progeny plant with itself or the second plant to produce one or more further progeny plants; and (d) selecting a further progeny plant comprising the clubroot resistant allele. In some aspects, step (c) comprises backcrossing. In other aspects, step (c) comprises 2 to 7 generations of backcrosses. In some aspects, step (d) comprises marker-assisted selection. In some aspects, these methods are used to produce a *B. napus* or *B. rapa* plant. In some aspects, these methods are used to select a plant from the group consisting of rutabaga, oil rape, Chinese cabbage, pak choi, and turnip. In some aspects, these methods are used to produce an inbred or a hybrid. In other aspects, these methods are used to produce a winter canola variety or a spring canola variety. In a further aspect, these methods are used to produce a winter canola variety. In some aspects, these methods are used to produce canola plants highly resistant, resistant, or moderately resistant to at least one *P. brassicae* pathotype selected from the group consisting of pathotypes 1 to 9, G, H, and 5x. In other aspects, canola plants produced by these methods are highly resistant, resistant, or moderately resistant to at least one *P. brassicae* pathotype selected from the group consisting of pathotypes 2, 3, 5, 5x, 6, 8, and G. In some aspects, these methods comprise using a marker assay, detecting a haplotype, assaying a SNP marker, or the use of an oligonucleotide probe. In other aspects, oligonucleotide probes used in these methods are adjacent to a polymorphic nucleotide position in the polymorphic locus.

In one aspect, this disclosure provides methods of selecting a canola plant with resistance to *P. brassicae* pathotype 5x, the methods comprising selecting a clubroot resistant allele at a polymorphic locus in a chromosomal segment flanked by any two of marker loci SEQ ID NOs: 1 to 8 on chromosome N3. In some aspects, these methods comprise detecting a clubroot resistant allele at a polymorphic locus within about 4 cM, 1 cM, 0.5 cM, or less than 0.5 cM of any one of marker loci SEQ ID NOs: 1-8. In other aspects, these methods comprise detecting a clubroot resistant allele at at least one polymorphic locus selected from the group consisting of SEQ ID NOs: 1-8. In some aspects, these methods are used to select a *B. napus* or *B. rapa* plant resistant to *P. brassicae* pathotype 5x. In other aspects, these methods are used to select a winter canola variety or a spring canola variety. In a further aspect, these methods are used to select a winter canola variety. In some aspects, these methods are used to select a plant from the group consisting of rutabaga, oil rape, Chinese cabbage, pak Choi, and turnip. In some aspects, these methods are used to select canola plants highly resistant, resistant, or moderately resistant to at least one *P. brassicae* pathotype selected from the group consisting of pathotypes 1 to 9, G, H, and 5x. In other aspects, canola plants selected by these methods are highly resistant, resistant, or moderately resistant to at least one *P. brassicae* pathotype selected from the group consisting of pathotypes 2, 3, 5, 5x, 6, 8, and G. In some aspects, these methods comprise using a marker assay, detecting a haplotype, assaying a SNP marker, or the use of an oligonucleotide probe. In other aspects, oligonucleotide probes used in these methods are adjacent to a polymorphic nucleotide position in the polymorphic locus.

In another aspect, this disclosure also provides methods of selecting a canola plant with resistance to *P. brassicae* pathotype 5x, the method comprising selecting a clubroot resistant allele at a polymorphic locus within 20 cM of any one of marker loci SEQ ID NOs: 1-8. In some aspects, these methods comprise detecting a clubroot resistant allele at a polymorphic locus within about 15 cM, 10 cM, 5 cM, 1 cM, 0.5 cM, or less than 0.5 cM of any one of marker loci SEQ ID NOs: 1-8. In other aspects, these methods comprise detecting a clubroot resistant allele at at least one polymorphic locus selected from the group consisting of SEQ ID NOs: 1-8. In some aspects, these methods are used to select a *B. napus* or *B. rapa* plant resistant to *P. brassicae* pathotype 5x. In other aspects, these methods are used to select a winter canola variety or a spring canola variety. In some aspects, these methods are used to select a plant from the group consisting of rutabaga, oil rape, Chinese cabbage, pak Choi, and turnip. In a further aspect, these methods are used to select a winter canola variety. In some aspects, these methods are used to select canola plants highly resistant, resistant, or moderately resistant to at least one *P. brassicae* pathotype selected from the group consisting of pathotypes 1 to 9, G, H, and 5x. In other aspects, canola plants selected by these methods are highly resistant, resistant, or moderately resistant to at least one *P. brassicae* pathotype selected from the group consisting of pathotypes 2, 3, 5, 5x, 6, 8, and G. In some aspects, these methods comprise using a marker assay, detecting a haplotype, assaying a SNP marker, or the use of an oligonucleotide probe. In other aspects, oligonucleotide probes used in these methods are adjacent to a polymorphic nucleotide position in the polymorphic locus.

In a further aspect, this disclosure provides methods of growing a canola plant in the presence of a spore of at least one pathotype of *P. brassicae*, the method comprising: (a) providing an elite spring canola seed comprising an introgressed clubroot resistance QTL in a chromosome interval flanked by any two of marker loci SEQ ID NOs: 1-8; (b) growing the elite spring canola seed in the presence of a spore of at least one pathotype of *P. brassicae*. In some aspects, these methods comprise growing elite canola seed in the presence of a spore of at least 2, 3, 4, 5, or 6 different pathotypes of *P. brassicae*. These pathotypes of *P. brassicae* can be selected from the group consisting of pathotypes 1 to 9 classified based on the differentials reported in Williams, *Phytopathology,* 56(6):624-626 (1966). In one aspect, methods disclosed herein are for growing a population of canola plants in a field comprising spores of at least one pathotype of *P. brassicae* selected from the group consisting of pathotypes 1 to 9.

A canola-growing field that comprises *P. brassicae* spores can be of any size. In some aspects, the canola-grow field has a size of greater than 25, 50, 100, 200, 500, 750, or 1000 acres. In other aspects, the canola-grow field is between 25 and 100, between 50 and 200, between 100 and 500, between 200 and 750, between 500 and 750, between 500 and 1000, or between 750 and 1000 acres.

In another aspect, this disclosure provides methods of growing a canola plant in the presence of a spore of *P. brassicae* pathotype 5x, the method comprising: (a) providing an elite canola seed comprising an introgressed clubroot resistance QTL in a chromosome interval flanked by any two of marker loci SEQ ID NOs: 1-8; (b) growing the elite canola seed in the presence of a spore of *P. brassicae* pathotype 5x. In one aspect, methods disclosed herein are for growing a population of canola plants in a field comprising spores of *P. brassicae* pathotype 5x.

In one aspect, this disclosure provides methods for introgressing a resistant allele of a locus conferring resistance to *P. brassicae* pathotype 5x, the method comprising (a) crossing a first canola plant with a second canola plant, wherein the first canola plant comprises the resistant allele; (b) genotyping a progeny plant from the cross using a marker associated with the resistant allele; and (c) selecting a progeny plant comprising the resistant allele. In some aspects, the introgressed resistant allele is present in, or from, canola variety Tosca. In other aspects, the marker associated with the resistant allele is within about 20 cM, 10 cM, 5 cM, 4 cM, 3 cM, 2 cM, 1 cM, 0.5 cM, or less than 0.5 cM of any one of marker loci SEQ ID NOs: 1-8. In some aspects, the second canola plant is a spring variety.

In one aspect, this disclosure provides methods for evaluating a collection of canola germplasm for resistance to *P. brassicae* pathotype 5x, the method comprising: (a) obtaining a collection of canola germplasm; (b) isolating nucleic acids from each germplasm of said collection; (c) assaying said nucleic acids for one or more markers closely linked to a QTL providing resistance to *P. brassicae* pathotype 5x; and (d) selecting germplasm having resistance to *P. brassicae* pathotype 5x based on said marker assay. In other aspects, the one or more markers closely linked to a QTL providing resistance to *P. brassicae* pathotype 5x are within about 20 cM, 10 cM, 5 cM, 4 cM, 3 cM, 2 cM, 1 cM, 0.5 cM, or less than 0.5 cM of any one of marker loci SEQ ID NOs: 1-8. In some aspects, the collection of canola germplasm comprises canola spring variety plants. In some aspects, the collection of canola germplasm consists of canola spring variety plants. In other aspects, these methods further comprise confirming the resistance of the germplasm selected based on markers by challenging the selected germplasm with a single spore isolate of *P. brassicae* pathotype 5x.

In one aspect, this disclosure provides elite spring canola plants comprising at least highly resistant, resistant, or clubroot resistance to *P. brassicae* pathotype 5x. In some aspects, these elite spring canola plants comprise a clubroot resistance locus in a chromosomal segment flanked by any two of marker loci SEQ ID NOs: 1 to 8 on chromosome N3 and this resistance locus confers resistance to pathotype 5x. In other aspects, these elite spring canola plants are further highly resistant, resistant, to or moderately resistant to at least one, at least two, at least three, or at least four *P. brassicae* pathotypes selected from the group consisting of pathotypes 1 to 9. In some aspects, these elite spring canola plants are from a species selected from the group consisting of *B. napus* and *B. rapa*.

In another aspect, this disclosure provides elite spring canola varieties comprising clubroot resistance conferred by a clubroot resistance locus in a chromosomal segment flanked by any two of marker loci SEQ ID NOs: 1 to 8 on chromosome N3. The clubroot resistance locus in the chromosomal segment flanked by any two of marker loci SEQ ID NOs: 1 to 8 can be either homozygous or heterozygous. In one aspect, these elite spring canola varieties are hybrids.

In one aspect, this disclosure provides an elite canola variety comprising clubroot resistance conferred by a clubroot resistance locus in a chromosomal segment flanked by any two of marker loci SEQ ID NOs: 1 to 8 on chromosome N3, wherein the variety is not Tosca. In a further aspect, this disclosure provides a single gene conversion canola line comprising one or more clubroot resistance loci disclosed herein. In some aspects, the converted single gene is a clubroot resistance locus in a chromosomal segment flanked by any two of marker loci SEQ ID NOs: 1 to 8 on chromosome N3.

In another aspect, this disclosure provides an elite transgenic canola plant or seed comprising an introgressed clubroot resistance quantitative trait locus (QTL), wherein the clubroot resistance QTL is from a chromosome interval flanked by any two of marker loci SEQ ID NOs: 1-8. In one aspect, the elite transgenic canola plant or seed provided herein is moderately resistant to clubroot. In another aspect, the elite transgenic canola plant or seed provided herein is resistant to clubroot. In another aspect, the elite transgenic canola plant or seed provided herein is highly resistant to clubroot.

In one aspect, this disclosure provides an elite hybrid canola seed comprising at least two clubroot resistance loci, wherein a first locus of the at least two clubroot resistance loci is in a chromosomal segment flanked by any two of marker loci SEQ ID NOs: 1 to 8 on chromosome N3, and wherein a canola plant from the seed comprises at least moderate resistance to at least one *P. brassicae* pathotype selected from the group consisting of pathotypes 1 to 9, G, and 5x. In some aspects, elite hybrid canola seeds provided herein comprise a resistance allele at at least one of marker loci SEQ ID NOs: 1-8. In other aspects, elite hybrid canola seeds provided herein comprise one or more clubroot resistance loci selected from the group consisting of Crr1, Crr2, Crr3, Crr4, CRa, CRb, CRc, and CRk. In further aspects, elite hybrid canola seeds provided herein comprise one or more clubroot resistance loci selected from the group consisting of PbBn-Korp-1, PbBn-Korp-2, PbBn-Korp-3, PbBn-Korp-4, PbBn-Korp-5, PbBn-k-1, PbBn-k-2, PbBn-k-3, PbBn-01.07-1, PbBn-01.07-2, PbBn-01.07-3, PbBn-1-1, PbBn-1-2, PbBn-01:60-1, PbBn-01:60-2, PbBn-01:60-3, PbBn-01:60-4, PbBn-e4x04-1, and PbBn-a-1.

In one aspect, this disclosure provides a container of elite spring canola seeds comprising at least moderate clubroot resistance to *P. brassicae* pathotype 5x. In another aspect, this disclosure provides a container of elite spring canola seeds comprising clubroot resistance conferred by a clubroot resistance locus in a chromosomal segment flanked by any two of marker loci SEQ ID NOs: 1 to 8 on chromosome N3. In a further aspect, this disclosure provides a container of elite transgenic canola seeds comprising an introgressed clubroot resistance quantitative trait locus (QTL), wherein the clubroot resistance QTL is from a chromosome interval flanked by any two of marker loci SEQ ID NOs: 1-8. In some aspects, these transgenic seeds are from a spring variety.

A container of canola seeds of the instant disclosure may contain any number, weight or volume of seeds. For example, a container can contain at least, or greater than, about 100, 200, 300, 400, 500, 600, 700, 800, 900, 1000, 1500, 2000, 2500, 3000, 3500, 4000 or more seeds. Alternatively, the container can contain at least, or greater than, about 1 ounce, 5 ounces, 10 ounces, 1 pound, 2 pounds, 3 pounds, 4 pounds, 5 pounds or more seeds. Containers of canola seeds may be any container available in the art. By way of non-limiting example, a container may be a box, a bag, a packet, a pouch, a tape roll, a tube, or a bottle.

In some aspects, elite canola plants provided herein are resistant to any one or more *P. brassicae* pathotypes selected from pathotypes 1 to 9, G, and 5x with a disease index (DI, see Example 1 for definition) of below 50%, 40%, 30%, 25%, 20%, 15%, 10%, or 5%. In other aspects, elite canola plants provided herein have a DI between 1% and 5%, between 5% and 10%, between 10% and 15%, between 15% and 20%, between 20% and 25%, between 25% and 30%, between 30% and 35%, between 35% and 40%, between 40% and 45%, between 45% and 50%, or between 50% and 55% against one or more *P. brassicae* pathotypes selected from pathotypes 1 to 9, G, and 5x.

In particular aspects, this disclosure provides elite canola spring varieties having a DI against *P. brassicae* pathotype 5x between 1% and 5%, between 5% and 10%, between 10% and 15%, between 15% and 20%, between 20% and 25%, between 25% and 30%, between 30% and 35%, between 35% and 40%, between 40% and 45%, between 45% and 50%, or between 50% and 55%. In other aspects, this disclosure provides elite canola spring varieties having a DI against *P. brassicae* pathotype 5x below 50%, 40%, 30%, 25%, 20%, 15%, 10%, or 5%. DI is calculated based on the formula as set forth in Example 1.

In some aspects, resistant alleles of clubroot resistance QTLs disclosed herein can be introgressed into a canola background susceptible to clubroot and confer clubroot disease resistance measured by a disease index reduction of at least 95%, 90%, 80%, 75%, 70%, 60%, 50%, 40%, 30%, 20%, or 10%. In other aspects, the disease index reduction from an introgressed clubroot resistance QTL disclosed herein is between 95% and 75%, between 90% and 70%, between 80% and 60%, between 75% and 50%, between 70% and 40%, between 60% and 30%, or between 50% and 20%.

In some aspects, the yield of elite canola plants comprising one or more introgressed clubroot resistance QTLs disclosed herein is comparable to canola plants in the same elite background without the introgressed QTLs. In one aspect, an elite spring canola plant comprising an introgressed clubroot resistance QTL disclosed herein has yield equal to greater than a canola plant in the same elite spring background without the clubroot resistance QTL. In some aspects, the yield of an elite spring canola variety comprising an clubroot resistance QTL introgression disclosed herein is about 1%, 2%, 3%, 4%, 5%, 7.5%, or 10% higher than the yield of the same elite spring canola background with the clubroot resistance QTL introgression. In other aspects, the yield of an elite spring canola variety comprising an clubroot resistance QTL introgression disclosed herein is between 0.5% and 2%, between 1% and 2%, between 1% and 3%, between 1% and 4%, between 1% and 5%, between 2% and 3%, between 2% and 4%, between 2% and 5%, between 3% and 4%, between 3% and 5%, or between 4% and 5% higher than the yield of the same elite spring canola background with the clubroot resistance QTL introgression.

In some aspects, methods or canola plants disclosed herein are used in combination with one or more pesticides including, but not limited to, herbicides, fungicides, insecticides, microbiocides, nematicides, insect repellents, bactericides, and other substances used to control pests. In other aspects, methods or canola plants disclosed herein are used in combination with one or more triazoles, strobilurins, acylamino acids, pyrimidines, pyridines, arylphenyl ketones, amides, benzanilides, imidazoles, dinitrophenols, morpholines, phenylsulfamides and organophosphorus cpds, derivatives thereof and combinations thereof which may be applied as seed, foliar, drench or drip treatments.

In one aspect, canola seeds disclosed herein can be subjected to various treatments. For example, the seeds can be treated to improve germination by priming the seeds or by disinfection to protect against seedborne pathogens. In another aspect, seeds can be coated with any available coating to improve, for example, plantability, seed emergence, and protection against seedborne pathogens. Seed coating can be any form of seed coating including, but not limited to, pelleting, film coating, and encrustments.

In a further aspect, the instant disclosure provides methods to enhance clubroot resistance in canola by combining two or more approaches selected from the group consisting of a) selecting a canola variety comprising one or more QTLs disclosed herein, b) crop rotation, c) liming of the soil, and d) application of fungicides. In some aspects, the combined approaches have synergistic effects in providing clubroot disease control.

In one aspect, this disclosure provides canola plant cells, tissues, and organs that are not reproductive material and do not mediate the natural reproduction of the plant. In another aspect, this disclosure also provides canola plant cells, tissues, and organs that are reproductive material and mediate the natural reproduction of the plant. In another aspect, this disclosure provides canola plant cells, tissues, and organs that cannot maintain themselves via photosynthesis. In another aspect, this disclosure provides somatic canola plant cells. Somatic cells, contrary to germline cells, do not mediate plant reproduction.

The provided cells, tissues and organs may be from seed, fruit, leaf, cotyledon, hypocotyl, meristem, embryos, endosperm, root, shoot, stem, pod, flower, infloresence, stalk, pedicel, style, stigma, receptacle, petal, sepal, pollen, anther, filament, ovary, ovule, pericarp, phloem, vascular tissue. In another aspect, this disclosure provides a canola plant chloroplast. In a further aspect, this disclosure provides epidermal cells, stomata cell, leaf or root hairs, a storage root, or a tuber. In another aspect, this disclosure provides a canola protoplast.

Skilled artisans understand that canola plants naturally reproduce via seeds, not via asexual reproduction or vegetative propagation. In one aspect, this disclosure provides canola endosperm. In another aspect, this disclosure provides canola endosperm cells. In a further aspect, this disclosure provides a male or female sterile canola plant, which cannot reproduce without human intervention.

In a further aspect, this disclosure provides processed products made from the disclosed canola plants. Such products include, but are not limited to, meal, oil, plant extract, starch, or fermentation or digestion products. In another aspect, this disclosure also provides a canola meal, which is substantially oil free and which is produced using the oilseed of any of the plants disclosed herein. In another aspect, this disclosure also provides a method of providing a canola meal by crushing oilseed of any of the plants disclosed herein.

In a further aspect, this disclosure provides canola meal or crude canola oil comprising a DNA molecule unique to a spring canola variety and further comprising a DNA molecule corresponding to a resistant allele from a chromosomal segment flanked by any two of marker loci SEQ ID NOs: 1 to 8.

Various canola lines disclosed herein can be used to transmit the clubroot QTL present in Tosca to new varieties using various cross pollination and selection methods. Breeders can also obtain hybrids using canola plants described here. Using standard crossing, backcrossing, and selection techniques, those of skill in the art may obtain commercial canola varieties with various desirable traits besides clubroot resistance. For example, breeders may obtain commercial canola lines with clubroot resistance and additional traits such as resistance to drought stress, frost tolerance (late spring or early fall frosts), elimination of green seed, high nutrient use efficiency, low saturated fatty acid content, new herbicide tolerance, additional disease resistance (e.g., seedling blight, brown girdling root rot), insect resistance (e.g., against root maggot or cabbage seedpod weevil), cold temperature tolerance for improved germination and emergence, larger seed size, improved winter hardiness and yield in winter canola, cytoplasmic male sterility, and higher yielding hybrids.

Canola plants or lines disclosed herein can also be genetically engineered to express various phenotypes of agronomic interest. Exemplary genes implicated in this regard include, but are not limited to, genes that confer resistance to pests or disease, genes that confer resistance or tolerance to an herbicide, genes modify oil content (e.g., elevated oleic acid via FAD-2 gene modification, decreased linolenic acid via FAD-3 gene modification, and altered conjugated linolenic or linoleic acid content), genes that control male sterility, genes that affect abiotic stress resistance, and other genes and transcription factors that affect plant growth and agronomic traits such as yield, flowering, plant growth or plant structure.

Canola Transformation

Canola plants disclosed herein can also be genetically transformed. Numerous methods for plant transformation have been developed including biological and physical plant transformation protocols. See, for example, Mild, et al., "Procedures for Introducing Foreign DNA into Plants" in *Methods in Plant Molecular Biology and Biotechnology*, Glick B. R. and Thompson, J. E. Eds. (CRC Press, Inc., Boca Raton, 1993) pages 67-88. In addition, expression vectors and in vitro culture methods for plant cell or tissue transformation and regeneration of plants are available. See, for example, Gruber, et al., "Vectors for Plant Transformation" in *Methods in Plant Molecular Biology and Biotechnology*, Glick B. R. and Thompson, J. E. Eds. (CRC Press, Inc., Boca Raton, 1993) pages 89-119.

A. *Agrobacterium*-Mediated Transformation—One method for introducing an expression vector into plants is based on the natural transformation system of *Agrobacterium*. See e.g., Horsch, et al., *Science* 227:1229 (1985). *A. tumefaciens* and *A. rhizogenes* are plant pathogenic soil bacteria which genetically transform plant cells. Descriptions of *Agrobacterium* vector systems and methods for *Agrobacterium*-mediated gene transfer are provided by, for example, U.S. Pat. No. 5,563,055 (Townsend and Thomas), incorporated herein by reference in its entirety.

B. Direct Gene Transfer—Several methods of plant transformation, collectively referred to as direct gene transfer, have been developed as an alternative to *Agrobacterium*-mediated transformation. A generally applicable method of plant transformation is microprojectile-mediated transformation wherein DNA is carried on the surface of microprojectiles. The expression vector is introduced into plant tissues with a biolistic device that accelerates the microprojectiles to speeds of 300 to 600 m/s which is sufficient to penetrate plant cell walls and membranes.

Another method for physical delivery of DNA to plants is sonication of target cells. Alternatively, liposome and spheroplast fusion have been used to introduce expression vectors into plants. Electroporation of protoplasts and whole cells and tissues can also be used.

Following transformation of canola target tissues, expression of the above-described selectable marker genes allows for preferential selection of transformed cells, tissues and/or plants, using regeneration and selection methods well-known in the art.

The foregoing methods for transformation would typically be used for producing a transgenic variety. The transgenic variety could then be crossed with another (non-transformed or transformed) variety, in order to produce a new transgenic variety. Alternatively, a genetic trait which has been engineered into a particular canola line using the foregoing transformation techniques could be moved into another line using traditional backcrossing techniques that are well-known in the plant breeding arts. For example, a backcrossing approach could be used to move an engineered trait from a public, non-elite variety into an elite variety, or from a variety containing a foreign gene in its genome into a variety or varieties which do not contain that gene.

Additional Breeding

Canola plants disclosed herein can also be subject to additional breeding using one or more known methods in the art, e.g., pedigree breeding, recurrent selection, mass selection, and mutation breeding. Pedigree breeding starts with the crossing of two genotypes, such as a canola variety comprising a clubroot resistance locus disclosed herein and another canola variety lacking such a resistance locus. If the two original parents do not provide all the desired characteristics, other sources can be included in the breeding population. In the pedigree method, superior plants are selfed and selected in successive filial generations. In the succeeding filial generations the heterozygous condition gives way to homogeneous varieties as a result of self-pollination and selection. Typically in the pedigree method of breeding, five or more successive filial generations of selfing and selection is practiced: $F_1$ to $F_2$; $F_2$ to $F_3$; $F_3$ to $F_4$; $F_4$ to $F_5$, etc. After a sufficient amount of inbreeding, successive filial generations will serve to increase seed of the developed variety. The developed variety may comprise homozygous alleles at about 95% or more of its loci.

In addition to being used to create a backcross conversion, backcrossing can also be used in combination with pedigree breeding. As discussed previously, backcrossing can be used to transfer one or more specifically desirable traits from one variety, the donor parent, to a developed variety called the recurrent parent, which has overall good agronomic characteristics yet lacks that desirable trait or traits. However, the same procedure can be used to move the progeny toward the genotype of the recurrent parent but at the same time retain many components of the non-recurrent parent by stopping the backcrossing at an early stage and proceeding with selfing and selection. For example, a canola variety may be crossed with another variety to produce a first generation progeny plant. The first generation progeny plant may then be backcrossed to one of its parent varieties to create a BC1 or BC2. Progeny are selfed and selected so that the newly developed variety has many of the attributes of the recurrent parent and yet several of the desired attributes of the non-recurrent parent. This approach leverages the value and strengths of the recurrent parent for use in new canola varieties.

Recurrent selection is a method used in a plant breeding program to improve a population of plants. The method entails individual plants cross pollinating with each other to form progeny. The progeny are grown and the superior progeny selected by any number of selection methods, which include individual plant, half-sib progeny, full-sib progeny and selfed progeny. The selected progeny are cross pollinated with each other to form progeny for another population. This population is planted and again superior plants are selected to cross pollinate with each other. Recurrent selection is a cyclical process and therefore can be repeated as many times as desired. The objective of recurrent selection is to improve the traits of a population. The improved population can then be used as a source of breeding material to obtain new varieties for commercial or breeding use, including the production of a synthetic line. A synthetic line is the resultant progeny formed by the intercrossing of several selected varieties.

Mass selection is another useful technique when used in conjunction with molecular marker enhanced selection. In mass selection seeds from individuals are selected based on phenotype or genotype. These selected seeds are then bulked and used to grow the next generation. Bulk selection requires growing a population of plants in a bulk plot, allowing the plants to self-pollinate, harvesting the seed in bulk and then using a sample of the seed harvested in bulk to plant the next generation. Also, instead of self pollination, directed pollination could be used as part of the breeding program.

Mutation breeding can also be used to introduce new traits into canola plants disclosed herein. Mutations that occur spontaneously or are artificially induced can be useful sources of variability for a plant breeder. The goal of artificial mutagenesis is to increase the rate of mutation for a desired characteristic. Mutation rates can be increased by many different means including temperature, long-term seed storage, tissue culture conditions, radiation; such as X-rays, Gamma rays (e.g. cobalt 60 or cesium 137), neutrons, (product of nuclear fission by uranium 235 in an atomic reactor), Beta radiation (emitted from radioisotopes such as phosphorus 32 or carbon 14), or ultraviolet radiation (from 2500 to 2900 nm), or chemical mutagens (such as base analogues (5-bromo-uracil), related compounds (8-ethoxy caffeine), antibiotics (streptonigrin), alkylating agents (sulfur mustards, nitrogen mustards, epoxides, ethylenamines, sulfates, sulfonates, sulfones, lactones), azide, hydroxylamine, nitrous acid, or acridines). Once a desired trait is observed through mutagenesis the trait may then be incorporated into existing germplasm by traditional breeding techniques.

Doubled Haploids

The production of double haploids can also be used for the development of canola plants with a homozygous phenotype in the breeding program. Canola plants disclosed herein or pregenies thereof can be used to produce double haploid plants. Double haploids are produced by the doubling of a set of chromosomes (1 N) from a heterozygous plant to produce a completely homozygous individual. For example, see Wan, et al., (1989) "Efficient Production of Doubled Haploid Plants Through Colchicine Treatment of Anther-Derived Maize Callus", *Theor. Appl. Genet.*, 77:889-892 and U.S. Pat. No. 7,135,615, incorporated herein by reference in its entirety. This can be advantageous because the process omits the generations of selfing needed to obtain a homozygous plant from a heterozygous source.

Thus, in some aspects, this disclosure provides methods for making a substantially homozygous canola plant by producing or obtaining a seed from a cross of a canola plant comprising a clubroot resistance allele and another canola plant and applying double haploid methods to the $F_1$ seed or $F_1$ plant or to any successive filial generation. Such methods would decrease the number of generations required to produce a variety in a desired background with a beneficial trait. See Bernardo, R. and Kahler, A. L., *Theor. Appl. Genet.* 102:986-992, 2001.

A pollination control system and effective transfer of pollen from one parent to the other offers improved plant breeding and an effective method for producing hybrid canola seed and plants. For example, the ogura cytoplasmic male sterility (cms) system, developed via protoplast fusion between radish (*Raphanus sativus*) and rapeseed (*Brassica napus*) is one of the most frequently used methods of hybrid production.

In developing improved new *Brassica* hybrid varieties, breeders can use self-incompatible (SI), cytoplasmic male sterile (CMS) and nuclear male sterile (NMS) *Brassica* plants as the female parent. In using these plants, breeders are attempting to improve the efficiency of seed production and the quality of the $F_1$ hybrids and to reduce the breeding costs. When hybridization is conducted without using SI, CMS or NMS plants, it is more difficult to obtain and isolate the desired traits in the progeny ($F_1$ generation) because the parents are capable of undergoing both cross-pollination and self-pollination. If one of the parents is a SI, CMS or NMS plant that is incapable of producing pollen, only cross pollination will occur. By eliminating the pollen of one parental variety in a cross, a plant breeder is assured of obtaining hybrid seed of uniform quality, provided that the parents are of uniform quality and the breeder conducts a single cross.

The present disclosure also provides production of hybrid seeds. The development of a canola hybrid in a canola plant breeding program involves three steps: (1) the selection of plants from various germplasm pools for initial breeding crosses; (2) the selfing of the selected plants from the breeding crosses for several generations to produce a series of inbred lines, which, although different from each other, breed true and are highly uniform; and (3) crossing the selected inbred lines with different inbred lines to produce the hybrids. During the inbreeding process in canola, the vigor of the lines decreases. Vigor is restored when two different inbred lines are crossed to produce the hybrid. An important consequence of the homozygosity and homogeneity of the inbred lines is that the hybrid between a defined pair of inbreds will always be the same. Once the inbreds that give a superior hybrid have been identified, the hybrid seed can be reproduced indefinitely as long as the homogeneity of the inbred parents is maintained.

In one aspect, production of $F_1$ hybrids includes crossing a CMS *Brassica* female parent, with a pollen producing male *Brassica* parent. To reproduce effectively, however, the male parent of the $F_1$ hybrid must have a fertility restorer gene (Rf gene). The presence of an Rf gene means that the $F_1$ generation will not be completely or partially sterile, so that either self-pollination or cross pollination may occur. Self pollination of the $F_1$ generation to produce several subsequent generations is important to ensure that a desired trait is heritable and stable and that a new variety has been isolated.

An example of a *Brassica* plant which is cytoplasmic male sterile and used for breeding is ogura (OGU) cytoplasmic male sterile (R. Pellan-Delourme and Renard, *Genome* 30:234-238 (1988)). A fertility restorer for ogura cytoplasmic male sterile plants has been transferred from *Raphanus sativus* (radish) to *Brassica* by Instit. National de Recherche Agricole (INRA) in Rennes, France. The restorer gene, Rfl originating from radish, is described in WO 92/05251. Improved versions of this restorer have been developed. For example, see WO 98/27806 "Oilseed *brassica* containing an improved fertility restorer gene for ogura cytoplasmic male sterility."

Other sources and refinements of CMS sterility in canola include the Polima cytoplasmic male sterile plant, as well as those of U.S. Pat. No. 5,789,566, "DNA sequence imparting cytoplasmic male sterility, mitochondrial genome, nuclear genome, mitochondria and plant containing said sequence and process for the preparation of hybrids"; U.S. Pat. No. 5,973,233 "Cytoplasmic male sterility system production canola hybrids"; and WO 97/02737 "Cytoplasmic male sterility system producing canola hybrids"; EP patent application 0 599042A "Methods for introducing a fertility restorer gene and for producing $F_1$ hybrids of *Brassica* plants thereby"; U.S. Pat. No. 6,229,072 "Cytoplasmic male sterility system production canola hybrids"; U.S. Pat. No. 4,658,085 "Hybridization using cytoplasmic male sterility, cytoplasmic herbicide tolerance, and herbicide tolerance from nuclear genes"; each of which is incorporated herein by reference in its entirety.

Further, as a result of the advances in sterility systems, lines are developed that can be used as an open pollinated variety (i.e. a pureline line sold to the grower for planting) and/or as a sterile inbred (female) used in the production of $F_1$ hybrid seed. In the latter case, favorable combining ability with a restorer (male) would be desirable. The resulting hybrid seed would then be sold to the grower for planting.

Combining ability of a line, as well as the performance of the line, is a factor in the selection of improved canola lines that may be used as inbreds. Combining ability refers to a line's contribution as a parent when crossed with other lines to form hybrids. The hybrids formed for the purpose of selecting superior lines are designated test crosses. One way of measuring combining ability is by using breeding values. Breeding values are based on the overall mean of a number of test crosses. This mean is then adjusted to remove environmental effects and it is adjusted for known genetic relationships among the lines.

Hybrid seed production requires inactivation of pollen produced by the female parent. Incomplete inactivation of the pollen provides the potential for self-pollination. This inadvertently self-pollinated seed may be unintentionally harvested and packaged with hybrid seed. Similarly, because the male parent is grown next to the female parent in the field there is also the potential that the male selfed seed could be unintentionally harvested and packaged with the hybrid seed. Once the seed from the hybrid bag is planted, it is possible to identify and select these self-pollinated plants. These self-pollinated plants will be genetically equivalent to one of the inbred lines used to produce the hybrid. Though the possibility of inbreds being included in hybrid seed bags exists, the occurrence is rare because much care is taken to avoid such inclusions. These self-pollinated plants can be identified and selected by one skilled in the art, either through visual or molecular methods.

Marker Detection

The present disclosure provides markers that are in linkage disequilibrium with at least one clubroot resistance loci and can be used to select for clubroot resistance. Exemplary markers comprise SEQ ID NOs: 1-8 with their resistance alleles are shown in Table 3. Markers within approximately 20 cM, 10 cM, 5 cM, 1 cM, 0.5 cM, or less than 0.5 cM of these exemplary markers can also be identified from the known art.

Genetic markers are distinguishable from each other (as well as from the plurality of alleles of any one particular marker) on the basis of polynucleotide length and/or sequence. A large number of canola molecular markers are known in the art, and are published or available from various sources, such as, Wang et al. *BMC Genomics* 2011, 12:101; Raman et al. *BMC Genomics* 2013, 14:277; Delourme et al. *BMC Genomics* 2013, 14:120; and references therein. In general, any differentially inherited polymorphic trait (including a nucleic acid polymorphism) that segregates among progeny is a potential genetic marker.

As a set, polymorphic markers serve as a useful tool for fingerprinting plants to inform the degree of identity of lines or varieties. These markers can form a basis for determining associations with phenotype and can be used to drive genetic gain. The implementation of marker-assisted selection is dependent on the ability to detect and analyze underlying genetic differences between individuals.

Herein, nucleic acid analysis methods include, but are not limited to, PCR-based detection methods, microarray methods, mass spectrometry-based methods and/or nucleic acid sequencing methods. In one aspect, the detection of polymorphic sites in a sample of DNA, RNA, or cDNA may be facilitated through the use of nucleic acid amplification methods. Such methods specifically increase the concentration of polynucleotides that span the polymorphic site, or include that site and sequences located either distal or proximal to it. Such amplified molecules can be readily detected by gel electrophoresis, fluorescence detection methods, or other means.

A method of achieving such amplification employs the polymerase chain reaction (PCR) using primer pairs that are capable of hybridizing to the proximal sequences that define a polymorphism in its double-stranded form. Methods for typing DNA based on mass spectrometry have been disclosed in U.S. Pat. Nos. 6,613,509 and 6,503,710, and references found therein.

Polymorphisms in DNA sequences can be detected or typed by a variety of effective methods well known in the art including, but not limited to, those disclosed in U.S. Pat. Nos. 5,468,613, 5,217,863; 5,210,015; 5,876,930; 6,030,787; 6,004,744; 6,013,431; 5,595,890; 5,762,876; 5,945,283; 5,468,613; 6,090,558; 5,800,944; 5,616,464; 7,312,039; 7,238,476; 7,297,485; 7,282,355; 7,270,981 and 7,250,252 all of which are incorporated herein by reference in their entireties. However, the compositions and methods of the present disclosure can be used in conjunction with any polymorphism typing method to type polymorphisms in genomic DNA samples. These genomic DNA samples used include but are not limited to genomic DNA isolated directly from a plant, cloned genomic DNA, or amplified genomic DNA.

For instance, polymorphisms in DNA sequences can be detected by hybridization to allele-specific oligonucleotide (ASO) probes as disclosed in U.S. Pat. Nos. 5,468,613 and 5,217,863. U.S. Pat. No. 5,468,613 discloses allele specific oligonucleotide hybridizations where single or multiple nucleotide variations in nucleic acid sequence can be detected in nucleic acids by a process in which the sequence containing the nucleotide variation is amplified, spotted on a membrane and treated with a labeled sequence-specific oligonucleotide probe.

Target nucleic acid sequence can also be detected by probe ligation methods as disclosed in U.S. Pat. No. 5,800,944 where sequence of interest is amplified and hybridized to probes followed by ligation to detect a labeled part of the probe.

Microarrays can also be used for polymorphism detection, wherein oligonucleotide probe sets are assembled in an overlapping fashion to represent a single sequence such that a difference in the target sequence at one point would result in partial probe hybridization (Borevitz et al., *Genome Res.* 13:513-523 (2003); Cui et al., *Bioinformatics* 21:3852-3858 (2005)). On any one microarray, it is expected there will be a plurality of target sequences, which may represent genes and/or noncoding regions wherein each target sequence is represented by a series of overlapping oligonucleotides, rather than by a single probe. This platform provides for high throughput screening a plurality of polymorphisms. A single-feature polymorphism (SFP) is a polymorphism detected by a single probe in an oligonucleotide array, wherein a feature is a probe in the array. Typing of target sequences by microarray-based methods is disclosed in U.S. Pat. Nos. 6,799,122; 6,913,879; and 6,996,476.

Target nucleic acid sequence can also be detected by probe linking methods as disclosed in U.S. Pat. No. 5,616,464, employing at least one pair of probes having sequences homologous to adjacent portions of the target nucleic acid sequence and having side chains which non-covalently bind to form a stem upon base pairing of the probes to the target nucleic acid sequence. At least one of the side chains has a photoactivatable group which can form a covalent cross-link with the other side chain member of the stem.

Other methods for detecting SNPs and Indels include single base extension (SBE) methods. Examples of SBE methods include, but are not limited to, those disclosed in U.S. Pat. Nos. 6,004,744; 6,013,431; 5,595,890; 5,762,876; and 5,945,283. SBE methods are based on extension of a nucleotide primer that is adjacent to a polymorphism to incorporate a detectable nucleotide residue upon extension of the primer. In certain aspects, the SBE method uses four synthetic oligonucleotides. Two of the oligonucleotides serve as PCR primers and are complementary to sequence of the locus of genomic DNA which flanks a region containing the polymorphism to be assayed. Following amplification of the region of the genome containing the polymorphism, the PCR product is mixed with the third and fourth oligonucleotides (called extension primers) which are designed to hybridize to the amplified DNA adjacent to the polymorphism in the presence of DNA polymerase and two differentially labeled dideoxynucleosidetriphosphates. If the polymorphism is present on the template, one of the labeled dideoxynucleosidetriphosphates can be added to the primer in a single base chain extension. The allele present is then inferred by determining which of the two differential labels was added to the extension primer. Homozygous samples will result in only one of the two labeled bases being incorporated and thus only one of the two labels will be detected. Heterozygous samples have both alleles present, and will thus direct incorporation of both labels (into different molecules of the extension primer) and thus both labels will be detected.

In another method for detecting polymorphisms, SNPs and Indels can be detected by methods disclosed in U.S. Pat. Nos. 5,210,015; 5,876,930; and 6,030,787 in which an oligonucleotide probe having a 5' fluorescent reporter dye and a 3' quencher dye covalently linked to the 5' and 3' ends of the probe. When the probe is intact, the proximity of the reporter dye to the quencher dye results in the suppression of the reporter dye fluorescence, e.g. by Forster-type energy transfer. During PCR, forward and reverse primers hybridize to a specific sequence of the target DNA flanking a polymorphism while the hybridization probe hybridizes to polymorphism-containing sequence within the amplified PCR product. In the subsequent PCR cycle DNA polymerase with 5'→3' exonuclease activity cleaves the probe and separates the reporter dye from the quencher dye resulting in increased fluorescence of the reporter.

In another aspect, the locus or loci of interest can be directly sequenced using nucleic acid sequencing technologies. Methods for nucleic acid sequencing are known in the art and include technologies provided by 454 Life Sciences (Branford, Conn.), Agencourt Bioscience (Beverly, Mass.), Applied Biosystems (Foster City, Calif.), LI-COR Biosciences (Lincoln, Nebr.), NimbleGen Systems (Madison, Wis.), Illumina (San Diego, Calif.), and VisiGen Biotechnologies (Houston, Tex.). Such nucleic acid sequencing technologies comprise formats such as parallel bead arrays, sequencing by ligation, capillary electrophoresis, electronic microchips, "biochips," microarrays, parallel microchips, and single-molecule arrays, as reviewed by Service, *Science* 311:1544-46 (2006).

In alternative aspects, in silico methods can be used to detect the marker loci of interest. For example, the sequence of a nucleic acid comprising the marker locus of interest can be stored in a computer. The desired marker locus sequence or its homolog can be identified using an appropriate nucleic acid search algorithm as provided by, for example, in such readily available programs as the Basic Local Alignment Search Tool (BLAST®), or even simple word processors.

Any of the aforementioned marker types can be employed in the context of the disclosure to identify chromosome intervals encompassing genetic element that contribute to superior agronomic performance (e.g., clubroot resistance).

The markers to be used in the methods of the present disclosure should preferably be diagnostic of origin in order for inferences to be made about subsequent populations. Experience to date suggests that SNP markers may be ideal for mapping because the likelihood that a particular SNP allele is derived from independent origins in the extant populations of a particular species is very low. As such, SNP markers appear to be useful for tracking and assisting introgression of QTL, particularly in the case of genotypes.

Association Mapping

In one aspect, the present disclosure provides chromosome intervals, marker loci, germplasm for conducting genome-wide association mapping for canola clubroot resistance. Exemplary chromosome intervals and marker loci are provided in Tables 2 to 4. Smaller intervals defined by any two marker loci disclosed in Tables 3 and 4 are also contemplated. Genome-wide association mapping is conducted to find signals of association for various complex traits by surveying genetic variation in the whole genome.

Association mapping relies on chromosomal recombination opportunities over a large number of generations, in the history of a species, which allows the removal of association between a QTL and any marker not tightly linked to it, thus improving the rate of discovery of true association (Jannink and Walsh, *Quantitative Genetics, Genomics and Plant Breeding*, Kang, Ed. CAB International, (2002) pp. 59-68).

An approach used to link phenotypic variation with genetic loci is marker-trait association (MTA) mapping, also known as linkage disequilibrium (LD) mapping. LD mapping emerged as an important gene mapping tool in early 1990's with the advent of high-throughput genotyping technology, and has been widely used in human genetics to identify genes affecting human diseases. This approach was introduced and began to be adopted in plant gene mapping studies in early 2000's (Flint-Garcia et al. (2003) *Annu Rev Plant Biol* 54: 357-374).

LD mapping assumes that the main cause for LD is linkage that binds loci on the same chromosome together in transmission to next generation. However, due to recombination events accumulated over many generations in a natural population, each chromosome has been shuffled deeply, so that the chromosome has been broken into many tiny regions where loci remain transmitted together, but loci from different regions tend to transmit independently as if they were from different chromosomes. Chromosomal regions where loci are bound together in transmission are commonly known as LD blocks (Reich et al. (2001) *Nature* 411:199-204). LD mapping identifies genes of interest through genetic markers on the LD blocks where the genes are located. This is done by detecting significant associations between the markers and the traits that the genes affect with a sample of unrelated individuals or a sample of unrelated pedigrees that are genotyped on a selected set of markers covering candidate gene regions or the whole genome, and phenotyped on a set of traits of interest.

Compared with traditional linkage mapping methods that are typically based on artificial biparental segregating populations (e.g., F2, BC, DH, RIL, etc.), LD mapping generally produces better mapping resolution, because of the smaller sizes of LD blocks. In addition, LD mapping is useful in identifying more than two functional alleles at associated markers in a germplasm. Further, LD mapping is efficient for evaluating natural populations.

Identification of QTL

A QTL can act through a single gene mechanism or by a polygenic mechanism. In some aspects, the present disclosure provides a QTL interval, where a QTL (or multiple QTLs) that segregates with disease resistance is contained in the chromosomal interval. As used herein, when a QTL (or multiple QTLs) segregates with disease resistance, it is referred to herein as a "resistance locus" (or "resistance loci").

In one aspect of this disclosure, the boundaries of QTL interval are drawn to encompass markers that will be linked to one or more QTLs. In other words, QTL interval is drawn such that any marker that lies within that interval (including the terminal markers that define the boundaries of the interval) is genetically linked to the QTL. Each interval comprises at least one QTL, and furthermore, may indeed comprise more than one QTL. Close proximity of multiple QTLs in the same interval may obfuscate the correlation of a particular marker with a particular QTL, as one marker may demonstrate linkage to more than one QTL. Conversely, e.g., if two markers in close proximity show co-segregation with the desired phenotypic trait, it is sometimes unclear if each of those markers identifying the same QTL or two different QTLs. Regardless, knowledge of how many QTLs are in a particular interval is not necessary to make or practice the claimed subject matter.

The statistical principles of QTL identification include penalized regression analysis, ridge regression, single point marker analysis, complex pedigree analysis, Bayesian MCMC, identity-by-descent analysis, interval mapping, composite interval mapping (CIM), and Haseman-Elston regression. Identification of QTL may be performed with the help of a computer and specialized software available from a variety of public and commercial sources known to those of skill in the art.

In some aspects, clubroot resistance QTLs disclosed herein are identified using the MQM (Multiple QTL Model) approach. This approach is implemented in three main steps: 1) missing genotypes are imputed and assigned a probability used as a weight in later analysis; 2) co-factors are selected genome-wide by multiple regression and backward elimination; and 3) QTL scan across the genome using the co-factors selected in step 2 (Arends et al., *Bioinformatics*, 26:2990-92 (2010)). QTL empirical significance threshold is estimated after 1000 permutations. The putative position of the QTL is estimated at the point of maximum LOD score. The QTL support interval is estimated using the Bayesian credible interval method. The phenotypic variance explained by a QTL is estimated as the square of the partial correlation coefficient ($R^2$) with the resistance score, adjusted for co-factors.

SNP markers are ideal for mapping because the likelihood that a particular SNP allele is derived from independent origins in the extant populations of a particular species is very low. As such, SNP markers are useful for tracking and assisting introgression of QTLs, particularly in the case of haplotypes.

The genetic linkage of additional marker molecules can be established by a gene mapping model such as, without limitation, the flanking marker model reported by Lander and Botstein, *Genetics*, 121:185-199 (1989), and the interval mapping, based on maximum likelihood methods described by Lander and Botstein, *Genetics*, 121:185-199 (1989), and implemented in the software package MAPMAKER/QTL (Lincoln and Lander, *Mapping Genes Controlling Quantitative Traits Using MAPMAKER/QTL*, Whitehead Institute for Biomedical Research, Massachusetts, (1990). Additional software includes Qgene, Version 2.23 (1996), Department of Plant Breeding and Biometry, 266 Emerson Hall, Cornell University, Ithaca, N.Y., the manual of which is herein incorporated by reference in its entirety).

A maximum likelihood estimate (MLE) for the presence of a marker is calculated, together with an MLE assuming no QTL effect, to avoid false positives. A $\log_{10}$ of an odds ratio (LOD) is then calculated as: LOD=$\log_{10}$ (MLE for the presence of a QTL/MLE given no linked QTL). The LOD score essentially indicates how much more likely the data are to have arisen assuming the presence of a QTL versus in its absence. The LOD threshold value for avoiding a false positive with a given confidence, say 95%, depends on the number of markers and the length of the genome. Graphs indicating LOD thresholds are set forth in Lander and Botstein, *Genetics*, 121:185-199 (1989), and further described by Arils and Moreno-González, *Plant Breeding*, Hayward, Bosemark, Romagosa (eds.) Chapman & Hall, London, pp. 314-331 (1993).

Additional models can be used. Many modifications and alternative approaches to interval mapping have been reported, including the use of non-parametric methods (Kruglyak and Lander, *Genetics*, 139:1421-1428 (1995), the entirety of which is herein incorporated by reference). Multiple regression methods or models can be also be used, in which the trait is regressed on a large number of markers (Jansen, *Biometrics in Plant Breed*, van Oijen, Jansen (eds.) Proceedings of the Ninth Meeting of the Eucarpia Section Biometrics in Plant Breeding, The Netherlands, pp. 116-124 (1994); Weber and Wricke, *Advances in Plant Breeding*, Blackwell, Berlin, 16 (1994)). Procedures combining interval mapping with regression analysis, whereby the phenotype is regressed onto a single putative QTL at a given marker interval, and at the same time onto a number of markers that serve as 'cofactors,' have been reported by Jansen and Stam, *Genetics*, 136:1447-1455 (1994) and Zeng, *Genetics*, 136:1457-1468 (1994). Generally, the use of cofactors reduces the bias and sampling error of the estimated QTL positions (Utz and Melchinger, *Biometrics in Plant Breeding*, van Oijen, Jansen (eds.) Proceedings of the Ninth Meeting of the Eucarpia Section Biometrics in Plant Breeding, The Netherlands, pp. 195-204 (1994)), thereby improving the precision and efficiency of QTL mapping (Zeng, *Genetics*, 136:1457-1468 (1994)). These models can be extended to multi-environment experiments to analyze genotype-environment interactions (Jansen et al., *Theo. Appl. Genet.* 91:33-37 (1995)).

In some aspects, the disclosure provides chromosomal intervals comprising QTL associated with clubroot resistance. The chromosome intervals of the disclosure are characterized in specific aspects by genomic regions including and flanked by any two of marker loci SEQ ID NOs: 1 to 8 on chromosome N3.

The disclosure also provides multiple markers linked to a QTL associated with clubroot resistance, for example, the markers having the sequence selected from SEQ ID NOs: 1-8. The disclosure therefore provides plants comprising a nucleic acid molecule selected from the group consisting of SEQ ID NOs: 1-8, fragments thereof, or complements thereof. The present disclosure further provides a plant comprising alleles of the chromosome interval linked to clubroot resistance or fragments and complements thereof as well as any plant comprising any combination of one or more clubroot resistant loci selected from the group consisting of SEQ ID NOs: 1-8. Plants provided by the disclosure may be homozygous or heterozygous for such alleles.

The compositions and methods of the present disclosure can be utilized to guide MAS or breeding canola varieties with a desired complement (set) of allelic forms of chromosome intervals associated with superior agronomic performance (e.g. clubroot resistance). Any of the disclosed marker alleles can be introduced into a canola line via introgression, by traditional breeding (or introduced via transformation, or both) to yield a canola plant with superior agronomic performance. The number of alleles associated with clubroot resistance that can be introduced or be present in a canola plant of the present disclosure ranges from 1 to the number of alleles disclosed herein, each integer of which is incorporated herein as if explicitly recited.

MAS using additional markers flanking either side of the DNA locus provide further efficiency because an unlikely double recombination event would be needed to simultaneously break linkage between the locus and both markers. Moreover, using markers tightly flanking a locus, one skilled in the art of MAS can reduce linkage drag by more accurately selecting individuals that have less of the potentially deleterious donor parent DNA. Any marker linked to or among the chromosome intervals described herein can thus find use within the scope of this disclosure.

These marker loci can be introgressed into any desired genomic background, germplasm, plant, line, variety, etc., as part of an overall MAS breeding program designed to enhance clubroot resistance. The disclosure also provides QTL intervals that can be used in MAS to select plants that demonstrate clubroot resistance. Similarly, QTL intervals can also be used to counter-select plants that are lacking clubroot resistance. By identifying plants lacking a desired marker locus, plants lacking clubroot resistance can be identified and selected or eliminated from subsequent crosses.

The present disclosure also extends to a method of making a progeny canola plant and the resulting progeny canola plants. In one aspect, the method comprises crossing a first parent canola plant with a second canola plant and growing the canola plant parent under plant growth conditions to yield canola plant progeny. Methods of crossing and growing canola plants are well within the ability of those of ordinary skill in the art. Such canola plant progeny can be assayed for alleles associated with clubroot resistance as disclosed herein and, thereby, the desired progeny selected. Such progeny plants or seed thereof can be sold commercially for canola production, used for food, processed to obtain a desired constituent of the canola, or further utilized in subsequent rounds of breeding. At least one of the first or second canola plants may be a canola plant of the present disclosure in that it comprises at least one of the allelic forms of the markers of the present disclosure, such that the progeny are capable of inheriting the allele.

By providing the positions in the canola genome of QTL intervals and the associated markers within those intervals, the disclosure also allows one skilled in the art to identify and use other markers within the intervals disclosed herein or linked to the intervals disclosed herein. Having identified such markers, these intervals can be readily identified from public linkage maps.

Closely linked markers flanking the locus of interest that have alleles in linkage disequilibrium (LD) with a clubroot resistant allele at that locus may be effectively used to select for progeny plants with clubroot resistance. Thus, the markers described herein, such as those listed in Tables 3 and 4, as well as other markers genetically linked to the same chromosome interval, may be used to select for canola plants with clubroot resistance. Often, a set of these markers will be used, (e.g., 2 or more, 3 or more, 4 or more, 5 or more) in the flanking regions of the locus. Optionally, as described above, a marker flanking or within the actual locus may also be used. The parents and their progeny may be screened for these sets of markers, and the markers that are polymorphic between the two parents used for selection. In an introgression program, this allows for selection of the gene or locus genotype at the more proximal polymorphic markers and selection for the recurrent parent genotype at the more distal polymorphic markers.

The choice of markers actually used to practice the disclosure is not limited and can be any marker that is genetically linked to the QTL intervals as described in Table 2, including markers within approximately 20 cM, 10 cM, 5 cM, 1 cM, 0.5 cM, or less than 0.5 cM of the intervals provided herein. Examples include, but are not limited to, any marker selected from SEQ ID NOs: 1-8. Furthermore, since there are many different types of marker detection assays known in the art, it is not intended that the type of marker detection assay used to practice this disclosure be limited in any way.

Marker Assisted Selection (MAS) Breeding

Marker loci and their resistance alleles provided herein can be used in MAS breeding of clubroot resistance. The more tightly linked a marker is with a DNA locus influencing a phenotype (e.g., clubroot resistance), the more reliable the marker is in MAS, as the likelihood of a recombination event unlinking the marker and the locus decreases. Markers containing the causal mutation for a trait, or that are within the coding sequence of a causative gene, are ideal as no recombination is expected between them and the sequence of DNA responsible for the phenotype. However, markers do not need to contain or correspond to causal mutations in order to be effective in MAS. In fact, most MAS breeding only uses markers linked to a causal mutation.

Developing molecular markers in crop species can increase efficiency in plant breeding through MAS. Genetic markers are used to identify plants that contain a desired genotype at one or more loci, and that are expected to transfer the desired genotype, along with a desired phenotype to their progeny. Genetic markers can be used to identify plants containing a desired genotype at one locus, or at several unlinked or linked loci (e.g., a haplotype), and that would be expected to transfer the desired genotype, along with a desired phenotype to their progeny. The present disclosure provides the means to identify plants that exhibit clubroot resistance by identifying chromosomal intervals and genetic markers associated with clubroot resistance.

In general, MAS uses polymorphic markers that have been identified as having a significant likelihood of co-segregation with a desired trait. Such markers are presumed to map near a gene or genes that give the plant its desired phenotype, and are considered indicators for the desired trait.

Identification of plants or germplasm that include a marker locus or marker loci linked to a desired trait or traits provides a basis for performing MAS. Plants that comprise favorable markers or favorable alleles are selected for, while plants that comprise markers or alleles that are negatively correlated with the desired trait can be selected against. Desired markers and/or alleles can be introgressed into plants having a desired (e.g., elite or exotic) genetic background to produce an introgressed plant or germplasm having the desired trait. In some aspects, it is contemplated that a plurality of markers for desired traits are sequentially or simultaneous selected and/or introgressed. The combinations of markers that are selected for in a single plant is not limited, and can include any combination of markers disclosed herein or any marker linked to the markers disclosed herein, or any markers located within the QTL intervals defined herein.

In some aspects, a first canola plant or germplasm exhibiting a desired trait (the donor, e.g., a disease resistant canola) can be crossed with a second canola plant or germplasm (the recipient, e.g., an elite or exotic canola, depending on characteristics that are desired in the progeny) to create an introgressed canola plant or germplasm as part of a breeding program. In some aspects, the recipient plant can also contain one or more loci associated with one or more desired traits, which can be qualitative or quantitative trait loci. In another aspect, the recipient plant can contain a transgene.

In some aspects, the recipient canola plant or germplasm will typically lack desired traits as compared to the first canola plant or germplasm, while the introgressed canola plant or germplasm will display improved traits as compared to the second plant or germplasm. An introgressed canola plant or germplasm produced by these methods are also a feature of this disclosure.

MAS is a powerful shortcut to select for desired phenotypes and for introgressing desired traits into cultivars (e.g., introgressing desired traits into elite lines). MAS is easily adapted to high throughput molecular analysis methods that can quickly screen large numbers of plant or germplasm genetic material for the markers of interest and is much more cost effective than cultivating and observing plants for visible traits.

When a population is segregating for multiple loci affecting one of multiple traits, e.g., multiple loci involved in clubroot resistance, the efficiency of MAS compared to phenotypic screening becomes even greater, because all of the loci can be evaluated together from a single sample of DNA.

Introgression of Clubroot Resistant Loci Using MAS

The instant disclosure provides methods and markers for introgressing a clubroot QTL present in Tosca into a new canola variety using MAS. This disclosure also contemplates introgression of the clubroot resistance QTL disclosed herein into other non-canola *Brassica* species, e.g., *B. oleracea*. Similarly, also contemplated is the introgression of the clubroot resistance QTL disclosed herein into *B. napus* vegetables (e.g., swedes, rutabaga, Siberian kale) or *B. rapa* vegetables (e.g., turnip, Chinese cabbage, pak Choi). Markers, haplotypes, and germplasm disclosed herein can also be used to introgress clubroot resistance loci into other *Brassica* species, e.g., *B. oleracea*, or *B. napus* or *B. rapa* vegetables.

Multiple methods are available to achieve the introgression. For example, introgression of a desired allele at a specified locus can be transmitted to at least one progeny via a cross between two parents of the same species, where at least one of the parents has the desired allele in its genome. Alternatively, for example, transmission of an allele can occur by recombination between two donor genomes, e.g., in a fused protoplast, where at least one of the donor protoplasts has the desired allele in its genome. The desired allele can be, e.g., a selected allele of a marker, a QTL, a transgene, or the like. In any case, offspring comprising the desired allele can be repeatedly backcrossed to a line having a desired genetic background and selected for the desired allele, to result in the allele becoming fixed in a selected genetic background.

The introgression of one or more desired loci from a donor line into another line is achieved via repeated backcrossing to a recurrent parent accompanied by selection to retain one or more loci from the donor parent. Markers associated with clubroot resistance are assayed in progeny and those progeny with one or more desired markers are selected for advancement. In another aspect, one or more markers can be assayed in the progeny to select for plants with the genotype of the agronomically elite parent.

It is generally anticipated that trait introgression activities will require more than one generation, wherein progeny are crossed to the recurrent (agronomically elite) parent or selfed. Selections are made based on the presence of one or more markers linked to clubroot resistance and can also be made based on the recurrent parent genotype, wherein screening is performed on a genetic marker and/or phenotype basis. In another aspect, markers of this disclosure can be used in conjunction with other markers, ideally at least one on each chromosome of the canola genome, to track the introgression of clubroot resistance into elite germplasm. In another aspect, QTL intervals associated with clubroot resistance will be useful in conjunction with SNP molecular markers of the present disclosure to combine quantitative and qualitative clubroot resistance in the same plant. It is within the scope of this disclosure to utilize the methods and compositions for trait integration of clubroot resistance. It is contemplated by the inventors that the present disclosure will be useful for developing commercial varieties with clubroot resistance and other agronomically elite phenotypes.

Canola plants or seeds disclosed herein can also be produced by one or more genome engineering techniques or subject to further genomic editing. For example, one or more clubroot resistance alleles can be introduced into another background (e.g., a susceptible background). Exemplary genome engineering techniques include meganucleases, Zinc-Finger nuclease, TALENs, and CRISPR-based system. See, e.g., Gaj et al., *Trends in Biotechnology*, 31(7):397-405 (2013). In one aspect, the present application provides a cisgenic canola plant exhibiting clubroot resistance. Used herein, "cisgenic" refers to genetic modification of a plant, plant cell, or plant genome in which all components (e.g., promoter, donor nucleic acid, and selection gene) have only plant origins. The plant component origins may be of the same or different plant species. In another aspect, a clubroot resistant cisgenic canola plant is developed by genome editing to carry a Tosca clubroot resistant allele. In other aspects, the Tosca clubroot resistance allele of a canola plant can be further modified using genomic editing.

The following are exemplary embodiments of the present disclosure.

Embodiment 1

A method for selecting a canola plant, the method comprising:
a. detecting in a population of canola plants a canola plant comprising a clubroot resistant allele at a polymorphic locus within 10 cM of any one of marker loci SEQ ID NOs: 1-8; and
b. selecting the canola plant comprising the clubroot resistant allele.

Embodiment 2

The method of embodiment 1, wherein said polymorphic locus is within about 5 cM, 4 cM, 3 cM, 2 cM, 1 cM, 0.5 cM, or less than 0.5 cM of any one of marker loci SEQ ID NOs: 1-8.

Embodiment 3

The method of embodiment 1, wherein said polymorphic locus comprises a sequence selected from the group consisting of SEQ ID NOs: 1-8.

Embodiment 4

The method of embodiment 1, wherein said selected canola plant is a *Brassica napus* plant.

Embodiment 5

The method of embodiment 4, wherein said *Brassica napus* plant is selected from the group consisting of rutabaga and oil rape.

Embodiment 6

The method of embodiment 1, wherein said selected canola plant is a *Brassica rapa* plant.

Embodiment 7

The method of embodiment 6, wherein said *Brassica rapa* plant is selected from the group consisting of Chinese cabbage, pak Choi, and turnip.

Embodiment 8

The method of embodiment 1, wherein said selected canola plant is from a winter canola variety.

Embodiment 9

The method of embodiment 1, wherein said selected canola plant is from a spring canola variety.

Embodiment 10

The method of embodiment 1, wherein said selected canola plant is highly resistant, resistant or moderately resistant to at least one *Plasmodiophora brassicae* pathotype selected from the group consisting of pathotypes 1 to 9, G, and 5x.

Embodiment 11

The method of embodiment 1, wherein said selected canola plant is resistant or moderately resistant to at least one *P. brassicae* pathotype selected from the group consisting of pathotypes 2, 3, 5, 5x, 6, 8, and G.

Embodiment 12

The method of embodiment 9, wherein said selected spring canola variety is resistant to at least one *P. brassicae* pathotype selected from the group consisting of pathotypes 2, 3, 5, 5x, 6, 8, and G.

Embodiment 13

The method of embodiment 1, wherein said method further comprises crossing a first canola plant comprising said clubroot resistant allele with a second canola plant to produce said population of canola plants.

Embodiment 14

The method of embodiment 13, wherein said method further comprises backcrossing to produce said population of canola plants.

Embodiment 15

The method of embodiment 1, wherein said step (a) comprises a marker assay.

Embodiment 16

The method of embodiment 1, wherein said step (a) comprises detecting a haplotype.

Embodiment 17

The method of embodiment 16, wherein said haplotype comprises resistance alleles of any two of marker loci SEQ ID NOs: 1-8.

Embodiment 18

The method of embodiment 1, wherein said step (a) comprises assaying a SNP marker.

Embodiment 19

The method of embodiment 1, wherein said step (a) comprises the use of an oligonucleotide probe.

Embodiment 20

The method of embodiment 19, wherein said oligonucleotide probe is adjacent to a polymorphic nucleotide position in said polymorphic locus.

Embodiment 21

The method of embodiment 1, further comprising producing a population of progenies from said selected canola plant.

Embodiment 22

A method of producing a canola plant with enhanced clubroot resistance, said method comprising:
a. crossing a first canola plant comprising a clubroot resistant allele with a second canola plant of a different genotype to produce one or more progeny plants; and
b. selecting a progeny plant comprising the clubroot resistant allele, wherein said clubroot resistant allele is in a chromosomal segment flanked by any two of marker loci SEQ ID NOs: 1 to 8.

Embodiment 23

The method of embodiment 22, wherein said polymorphic locus is within about 4 cM, 3 cM, 2 cM, 1 cM, 0.5 cM, or less than 0.5 cM of any one of marker loci SEQ ID NOs: 1-8.

Embodiment 24

The method of embodiment 22, wherein said polymorphic locus comprises a sequence selected from the group consisting of SEQ ID NOs: 1-8.

Embodiment 25

The method of embodiment 22, further comprising:
c. developing a doubled haploid plant from a microspore of the selected progeny plant.

Embodiment 26

The method of embodiment 25, further comprising:
d. backcrossing the doubled haploid plant with the second canola plant.

Embodiment 27

The method of embodiment 22, further comprising:
c. crossing the selected progeny plant with itself or the second plant to produce one or more further progeny plants; and
d. selecting a further progeny plant comprising the clubroot resistant allele.

Embodiment 28

The method of embodiment 26, wherein step (d) of selecting comprises marker-assisted selection.

Embodiment 29

The method of embodiment 28, wherein said marker-assisted selection comprises selecting a marker within about 4 cM, 3 cM, 2 cM, 1 cM, 0.5 cM, or less than 0.5 cM of any one of marker loci SEQ ID NOs: 1-8.

Embodiment 30

The method of embodiment 26, wherein said production of said one or more further progeny plants comprises backcrossing.

Embodiment 31

The method of embodiment 30, wherein said backcrossing comprises 2 to 7 generations of backcrosses.

Embodiment 32

The method of embodiment 22, wherein said first canola plant is an inbred or a hybrid.

Embodiment 33

The method of embodiment 22, wherein said second canola plant is an agronomically elite canola plant.

Embodiment 34

A method for creating a population of canola plants with clubroot resistance, said method comprising:
a. genotyping a first population of canola plants with a marker closely linked to a first clubroot resistance locus and with a marker closely linked to a second clubroot resistance locus, wherein said first clubroot resistance locus is located in a chromosomal segment flanked by any two of marker loci SEQ ID NOs: 1 to 8;
b. selecting from the first population one or more canola plants containing said first and second clubroot resistance loci; and
c. producing a population of offspring from the selected one or more canola plants.

Embodiment 35

The method of embodiment 34, wherein said second clubroot resistance locus is selected from the group consisting of Crr1, Crr2, Crr3, Crr4, CRa, CRb, CRc, CRk.

Embodiment 36

The method of embodiment 34, wherein said second clubroot resistance locus is selected from the group consisting of PbBn-Korp-1, PbBn-Korp-2, PbBn-Korp-3, PbBn-Korp-4, PbBn-Korp-5, PbBn-k-1, PbBn-k-2, PbBn-k-3, PbBn-01.07-1, PbBn-01.07-2, PbBn-01.07-3, PbBn-1-1, PbBn-1-2, PbBn-01:60-1, PbBn-01:60-2, PbBn-01:60-3, PbBn-01:60-4, PbBn-e4x04-1, and PbBn-a-1.

Embodiment 37

The method of embodiment 34, wherein said second clubroot resistance locus is located in a chromosomal segment flanked by any two of marker loci SEQ ID NOs: 9 to 12.

Embodiment 38

The method of embodiment 34, wherein said second clubroot resistance locus is within about 20 cM, 10 cM, 5 cM, 4 cM, 3 cM, 2 cM, 1 cM, 0.5 cM, or less than 0.5 cM of any one of marker loci SEQ ID NOs: 9 to 12.

Embodiment 39

A method of selecting a canola plant with resistance to *P. brassicae* pathotype 5x, said method comprising selecting a clubroot resistant allele at a polymorphic locus in a chromosomal segment flanked by any two of marker loci SEQ ID NOs: 1 to 8.

Embodiment 40

A method of selecting a canola plant with resistance to *P. brassicae* pathotype 5x, said method comprising selecting a clubroot resistant allele at a polymorphic locus within 10 cM of any one of marker loci SEQ ID NOs: 1-8.

Embodiment 41

The method of embodiment 40, wherein said polymorphic locus is within about 5 cM, 4 cM, 3 cM, 2 cM, 1 cM, 0.5 cM, or less than 0.5 cM of any one of marker loci SEQ ID NOs: 1-8.

Embodiment 42

The method of embodiment 40, wherein said polymorphic locus comprises a sequence selected from the group consisting of SEQ ID NOs: 1-8.

Embodiment 43

A method of growing a canola plant in the presence of a spore of at least one pathotype of *P. brassicae*, said method comprising:
a. providing a spring canola seed comprising an introgressed clubroot resistance QTL in a chromosome interval flanked by any two of marker loci SEQ ID NOs: 1-8;
b. growing the spring canola seed in the presence of a spore of at least one pathotype of *P. brassicae*.

Embodiment 44

The method of embodiment 43, wherein said at least one pathotype is selected from the group consisting of pathotypes 1 to 9, G, and 5x.

Embodiment 45

The method of embodiment 43, wherein said canola plant is grown in a field.

Embodiment 46

The method of embodiment 43, wherein said spring canola seed is from an agronomically elite canola variety.

Embodiment 47

A method of growing a canola plant in the presence of a spore of *P. brassicae* pathotype 5x, said method comprising:
a. providing a canola seed comprising an introgressed clubroot resistance QTL in a chromosome interval flanked by any two of marker loci SEQ ID NOs: 1-8;
b. growing the canola seed in the presence of a spore of *P. brassicae* pathotype 5x.

Embodiment 48

A spring canola variety comprising clubroot resistance conferred by a clubroot resistance locus in a chromosomal segment flanked by any two of marker loci SEQ ID NOs: 1 to 8.

Embodiment 49

The spring canola variety of embodiment 48, wherein said variety is resistant to or moderately resistant to at least one, at least two, or at least three *P. brassicae* pathotypes selected from the group consisting of pathotypes 1 to 9, G, and 5x.

Embodiment 50

The spring canola variety of embodiment 48, wherein said variety is resistant to or moderately resistant *P. brassicae* pathotype 5x.

Embodiment 51

The spring canola variety of embodiment 48, wherein said variety is homozygous at said clubroot resistance locus.

Embodiment 52

The spring canola variety of embodiment 48, wherein said variety is heterozygous at said clubroot resistance locus.

Embodiment 53

The spring canola variety of embodiment 48, wherein said variety is an elite canola variety.

Embodiment 54

A spring canola variety comprising clubroot resistance conferred by a clubroot resistance locus within about 20 cM, 10 cM, 5 cM, 4 cM, 3 cM, 2 cM, 1 cM, 0.5 cM, or less than 0.5 cM of any one of marker loci SEQ ID NOs: 1-8.

Embodiment 55

The spring canola variety of embodiment 54, wherein said variety is resistant to or moderately resistant to at least one, at least two, or at least three *P. brassicae* pathotypes selected from the group consisting of pathotypes 1 to 9, G, and 5x.

Embodiment 56

The spring canola variety of embodiment 54, wherein said variety is resistant to or moderately resistant *P. brassicae* pathotype 5x.

Embodiment 57

The spring canola variety of embodiment 54, wherein said variety is an elite canola variety.

Embodiment 58

A canola variety comprising clubroot resistance conferred by a clubroot resistance locus in a chromosomal segment flanked by any two of marker loci SEQ ID NOs: 1 to 8, wherein said variety is not Tosca.

Embodiment 59

A transgenic canola plant or seed comprising an introgressed clubroot resistance quantitative trait locus (QTL), wherein said clubroot resistance QTL is from a chromosome interval flanked by any two of marker loci SEQ ID NOs: 1-8.

Embodiment 60

The transgenic canola plant or seed of embodiment 59, wherein said canola plant is moderately resistant to clubroot.

Embodiment 61

The transgenic canola plant or seed of embodiment 59, wherein said canola plant is resistant to clubroot.

Embodiment 62

The transgenic canola plant or seed of embodiment 59, wherein said canola plant is resistant or moderately resistant to at least one *P. brassicae* pathotype selected from the group consisting of types 1 to 9, G, and 5x.

Embodiment 63

The transgenic canola plant of embodiment 59, wherein said canola plant is a hybrid.

Embodiment 64

The transgenic canola plant of embodiment 59, wherein said canola plant is a inbred.

Embodiment 65

The transgenic canola plant of embodiment 59, wherein said canola plant is from an elite canola variety.

Embodiment 66

A transgenic canola plant or seed comprising an introgressed clubroot resistance quantitative trait locus (QTL), wherein said clubroot resistance QTL is within about 20 cM, 10 cM, 5 cM, 4 cM, 3 cM, 2 cM, 1 cM, 0.5 cM, or less than 0.5 cM of any one of marker loci SEQ ID NOs: 1-8.

Embodiment 67

A hybrid canola seed comprising at least two clubroot resistance loci, wherein a first locus of said at least two clubroot resistance loci is in a chromosomal segment flanked by any two of marker loci SEQ ID NOs: 1 to 8, and wherein a canola plant from said seed comprises at least moderate resistance to at least one *P. brassicae* pathotype selected from the group consisting of pathotypes 1 to 9, G, and 5x.

Embodiment 68

The canola plant of embodiment 67, wherein said canola plant comprises a resistance allele at at least one of marker loci SEQ ID NOs: 1-8.

Embodiment 69

The canola plant of embodiment 67, wherein said plant comprises a second clubroot resistance locus selected from the group consisting of Crr1, Crr2, Crr3, Crr4, CRa, CRb, CRc, and CRk.

Embodiment 70

The canola plant of embodiment 67, wherein said plant comprises a second clubroot resistance locus located in a chromosomal segment flanked by any two of marker loci SEQ ID NOs: 9 to 12.

Embodiment 71

The canola plant of embodiment 67, wherein said plant comprises a second clubroot resistance locus within about 20 cM, 10 cM, 5 cM, 4 cM, 3 cM, 2 cM, 1 cM, 0.5 cM, or less than 0.5 cM of any one of marker loci SEQ ID NOs: 9 to 12.

Embodiment 72

A method for introgressing a resistant allele of a locus conferring resistance to *P. brassicae* pathotype 5x, said method comprising:
a. crossing a first canola plant with a second canola plant, wherein the first canola plant comprises said resistant allele;
b. genotyping a progeny plant from the cross using a marker associated with said resistant allele; and
c. selecting a progeny plant comprising the resistant allele.

Embodiment 73

The method of embodiment 72, wherein said resistant allele is present in canola variety Tosca.

Embodiment 74

The method of embodiment 72, wherein said marker is within about 20 cM, 10 cM, 5 cM, 4 cM, 3 cM, 2 cM, 1 cM, 0.5 cM, or less than 0.5 cM of any one of marker loci SEQ ID NOs: 1-8.

Embodiment 75

A method for evaluating a collection of canola germplasm for resistance to *P. brassicae* pathotype 5x, said method comprising:

a. obtaining a collection of canola germplasm;
b. isolating nucleic acids from each germplasm of the collection;
c. assaying the nucleic acids for one or more markers closely linked to a QTL providing resistance to *P. brassicae* pathotype 5x;
d. selecting germplasm having resistance to *P. brassicae* pathotype 5x based on said marker assay.

Embodiment 76

The method of embodiment 75, wherein said one or more markers are within about 20 cM, 10 cM, 5 cM, 4 cM, 3 cM, 2 cM, 1 cM, 0.5 cM, or less than 0.5 cM of any one of marker loci SEQ ID NOs: 1-8.

Embodiment 77

The method of embodiment 75, wherein said method further comprises confirming the resistance of said selected germplasm by challenging said germplasm with a single spore isolate of *P. brassicae* pathotype 5x.

EXAMPLES

Example 1. Evaluation of Clubroot Resistance in *Brassica napus* by Assessing Disease Index A disease index (DI) model is used to evaluate canola plants' resistance to clubroot in an infection assay. For this assay, *Brassica napus* plants are inoculated at the time of planting by covering fungicide-treated seeds with a layer of cover soil mix containing ground galls. The potted plants are incubated in a growth chamber for approximately 5 to 6 weeks. At the four-leaf stage, the plants are rated for their clubroot resistance. The plant along with its soil is carefully removed from the pot and the roots are washed. Clubroot is rated based on the size and number of galls on the roots (0-3 rating scale; Table 1).

TABLE 1

Rating scale for relative clubroot resistance

| Disease Rating | Description |
| --- | --- |
| 0 | No galling |
| 1 | A few small galls (small galls on less than ⅓ of root) |
| 2 | Moderate galling (small to medium-sized galls on ⅓ to ⅔ of root |
| 3 | Severe galling (medium to large-sized galls on more than ⅔ of root) |

The disease index (DI) is calculated according to the formula $$DI = \frac{\sum (0n_0 + 1n_1 + 2n_2 + 3n_3)}{3N} 100$$

with $n_0$ through $n_3$ being the number of plants in each class showing an infection rating of 0 through 3 and N being the total number of plants tested.

Example 2. Marker Trait Association Studies of Clubroot Root Resistance in Canola Variety Tosca To investigate the clubroot root resistance in canola variety Tosca, Tosca is crossed as a female parent with a clubroot susceptible canola variety PR9040 (a spring canola, *Brassica napus*). A doubled-haploid (DH) population (DH1; n=250) is developed from microspores of an $F_1$ plant of the Tosca×PR9040 cross. The DH1 plants are evaluated for their clubroot resistance as described in Example 1. Leaf tissue samples are taken from the DH1 plants and DNA is extracted for genotyping. The DNA samples are genotyped with more than 40,000 Infinium markers. A total of 7689 polymorphic markers are identified between Tosca and PR9040, and are used for QTL mapping analysis. These markers span 2513 cM with an average of one marker every 0.3 cM across the genome.

The phenotypic data are analyzed for any influential outliers, and variance component estimation is used to estimate repeatability (calculated to be 99%). The resistant-susceptible (92-106) segregation ratio in the DH1 population is statistically consistent with a Mendelian 1:1 segregation ratio. Disease rating and disease index both show a bimodal distribution. The disease index, ordinal rating, and binary rating scales data are used for QTL analysis, which is completed using the R/qtl package (Broman et al., *Bioinformatics*, 19:889-90, (2003)).

The MQM (Multiple QTL Model) approach is implemented in three main steps: 1) missing genotypes are imputed and assigned a probability used as a weight in later analysis; 2) co-factors are selected genome-wide by multiple regression and backward elimination; and 3) QTL scan across the genome using the co-factors selected in step 2 (Arends et al., *Bioinformatics*, 26:2990-92 (2010)). The QTL empirical significance threshold is estimated after 1000 permutations. The putative position of the QTL is estimated at the point of maximum LOD score. The QTL support interval is estimated using the Bayesian credible interval method. The phenotypic variance explained by a QTL is estimated as the square of the partial correlation coefficient ($R^2$) with the resistance score, adjusted for co-factors.

A single significant QTL is identified on chromosome N3. The QTL is located within a 4 cM support interval (Table 2). The clubroot QTL identified in Tosca differs (about 52 cM apart) from a Mendel-derived clubroot resistance locus on chromosome N3 previously identified by Monsanto (FIG. 1). Examplary markers associated with the Mendel-derived clubroot resistance locus is listed in Table 4.

TABLE 2

An interval on Tosca's Chromosome N3 comprise a single significant QTL for clubroot resistance.

| | | | Left flanking marker | | Right flanking marker | | | | | |
|---|---|---|---|---|---|---|---|---|---|---|
| Chr | QTL peak (cM) | QTL interval (cM) | Name | Pos. (cM) | Name | Pos. (cM) | p val. | LOD | Add. Effect | PVE (%) |
| N3 | 118.4 | 116-120 | SEQ ID NO. 3 | 116 | SEQ ID NO. 4 | 119 | 7.20E−12 | 53 | 1.3 | 71 |

TABLE 3

Exemplary SNP markers from Tosca clubroot resistance QTL interval including primers and probes from the markers.

| Chr. | Position (cM) | Marker SEQ ID | Length | SNP Position | Example Resistant Allele | Example Susceptible Allele | Forward Primer SEQ ID | Reverse Primer SEQ ID | VIC Probe SEQ ID | FAM Probe SEQ ID | p-value | Prob (R\|A)* | OR** | Physical position on B. napus Damor map |
|---|---|---|---|---|---|---|---|---|---|---|---|---|---|---|
| N3 | 116 | 1 | 121 | 61 | G | A | 13 | 14 | 15 | 16 | 1.94E−15 | 0.968 | 1545 | 13,912,908 |
| N3 | 116 | 2 | 121 | 61 | C | T | 17 | 18 | 19 | 20 | 1.03E−15 | 0.947 | 909 | 13,757,171 |
| N3 | 116 | 3 | 121 | 61 | A | G | 21 | 22 | 23 | 24 | 1.60E−14 | 0.978 | 2340 | 13,929,151 |
| N3 | 119 | 4 | 121 | 61 | G | A | 25 | 26 | 27 | 28 | 7.23E−12 | 0.989 | 4680 | 14,291,837 |
| N3 | 119 | 5 | 301 | 150 | G | A | 29 | 30 | 31 | 32 | 1.24E−11 | 0.987 | 2670 | 14,387,215 |
| N3 | 119 | 6 | 121 | 61 | G | A | 33 | 34 | 35 | 36 | 9.77E−12 | 0.989 | 4443 | 14,383,243 |
| N3 | 119 | 7 | 121 | 61 | A | C | 37 | 38 | 39 | 40 | 5.48E−12 | 0.989 | 3044 | 14,389,227 |
| N3 | 119 | 8 | 121 | 61 | n/a | n/a | — | — | — | — | 6.84E−12 | 0.989 | 4727 | 14,343,253 |

*Probability of resistance in presence of Tosca allele;
**Odds ratio

TABLE 4

Exemplary SNP markers from Mendel clubroot resistance QTL interval including primers and probes from the markers

| Chr. | Position (cM) | Marker SEQ ID | Length | SNP Position | Example Resistant Allele | Example Susceptible Allele | Forward Primer SEQ ID | Reverse Primer SEQ ID | VIC Probe SEQ ID | FAM Probe SEQ ID | p-value | LOD | Physical position on B. napus Damor map |
|---|---|---|---|---|---|---|---|---|---|---|---|---|---|
| N3 | 136 | 9 | 276 | 201 | T | C | 41 | 42 | 43 | 44 | <1e−5 | 13.3 | 22,488,138 |
| N3 | 139.8 | 10 | 279 | 139 | G | A | 45 | 46 | 47 | 48 | <1e−5 | 15.3 | 22,784,402 |
| N3 | 139.8 | 11 | 537 | 109 | C | A | 49 | 50 | 51 | 52 | <1e−5 | 15.3 | 23,013,911 |
| N3 | 139.8 | 12 | 441 | 291 | C | G | 53 | 54 | 55 | 56 | <1e−5 | 15.3 | 23,200,257 |

Example 3. Evaluating Efficacy of the Clubroot QTL Present in Tosca

The clubroot QTL present in Tosca is analyzed for its clubroot resistance efficacy. The DH progenies are classified based on the eight markers associated with the clubroot QTL present in Tosca (Table 3). Plants are grouped as "positive" if they carry the same genotype as Tosca within the QTL interval and "negative" if they carry the same genotype as PR9040 within the QTL interval. The efficacy of the QTL is evaluated based on differences of clubroot disease rating and disease index between the positive group and negative group. T-test is performed to test if the efficacy is significantly different between the positive and negative groups based on a p-value cutoff of 0.05.

A significant difference is observed for both disease rating and disease index between the positive and negative groups (Table 5). Lines carrying favorable alleles (resistant alleles) from Tosca provide a reduction of 2.66 points based on the 0-3 phenotype rating (described in Example 1) or a 88.66% disease index reduction compared to lines carrying the unfavorable alleles (susceptible alleles) from PR9040. This observation indicates that the QTL present in Tosca can be used to reduce the disease rating by 2.66 points or to reduce the disease index by 88.66% if the QTL is introgressed into lines susceptible to clubroot.

TABLE 5

Clubroot disease rating and disease index reduction conferred by a Tosca clubroot QTL.

| | Rating | Disease Index |
|---|---|---|
| Efficacy | 2.66 | 88.66 |
| P-value | 1.35E−96 | 1.35E−96 |

Example 4. The Clubroot QTL Present in Tosca is Effective Against P. brassicae Pathotypes 2, 3, 5, 5x, 6, 8, and G Clubroot resistance can be pathotype specific. To determine the pathotype specificity of the clubroot QTL present in Tosca, one week-old seedlings are inoculated and screened against pathotypes 2, 3, 5, 5X, 6, 8, G and H. These pathotypes are classified based on the differentials reported in Williams, *Phytopathology*, 56(6):624-26 (1966). Resting spores of *P. brassicae* are maintained on canola and stored as frozen root galls at −20° C. until needed. Resting spores are extracted from the frozen galls as described by Strelkov et al. (2006), and adjusted to a concentration of 1.0×10⁷ resting spores/mL. The single-spore isolates SACAN-ss3 (pathotype 2), SACAN-ss1 (pathotype 3), ORCA-ss4 (pathotype 5), AbotJE-ss1 (pathotype 6) and CDCN-ss2 (pathotype 8) are used in the screening (Xue et al., 2008), along with a mixture (in equal amounts) of the field populations L-G1, L-G2 and L-G3, representing pathotype 5x.

The seedlings are pre-germinated on a piece of moistened filter paper in Petri dishes, and inoculated by dipping the entire root system in a resting spore suspension for 10 seconds. The inoculated seedlings are then immediately planted in 6×6×6 cm plastic pots filled with Sunshine LA4 potting mixture at a density of one seedling per pot. The pots are thoroughly watered and transferred to a greenhouse at 21±2° C. with a 16 h/8 h photoperiod. The potting mixture in the pots is kept saturated with water (pH 6.5) for the first week after inoculation and then watered and fertilized as required. Twelve seedlings of each host line are inoculated with each *P. brassicae* population and inoculation is repeated for a total of four time per genotype.

Figure 2:
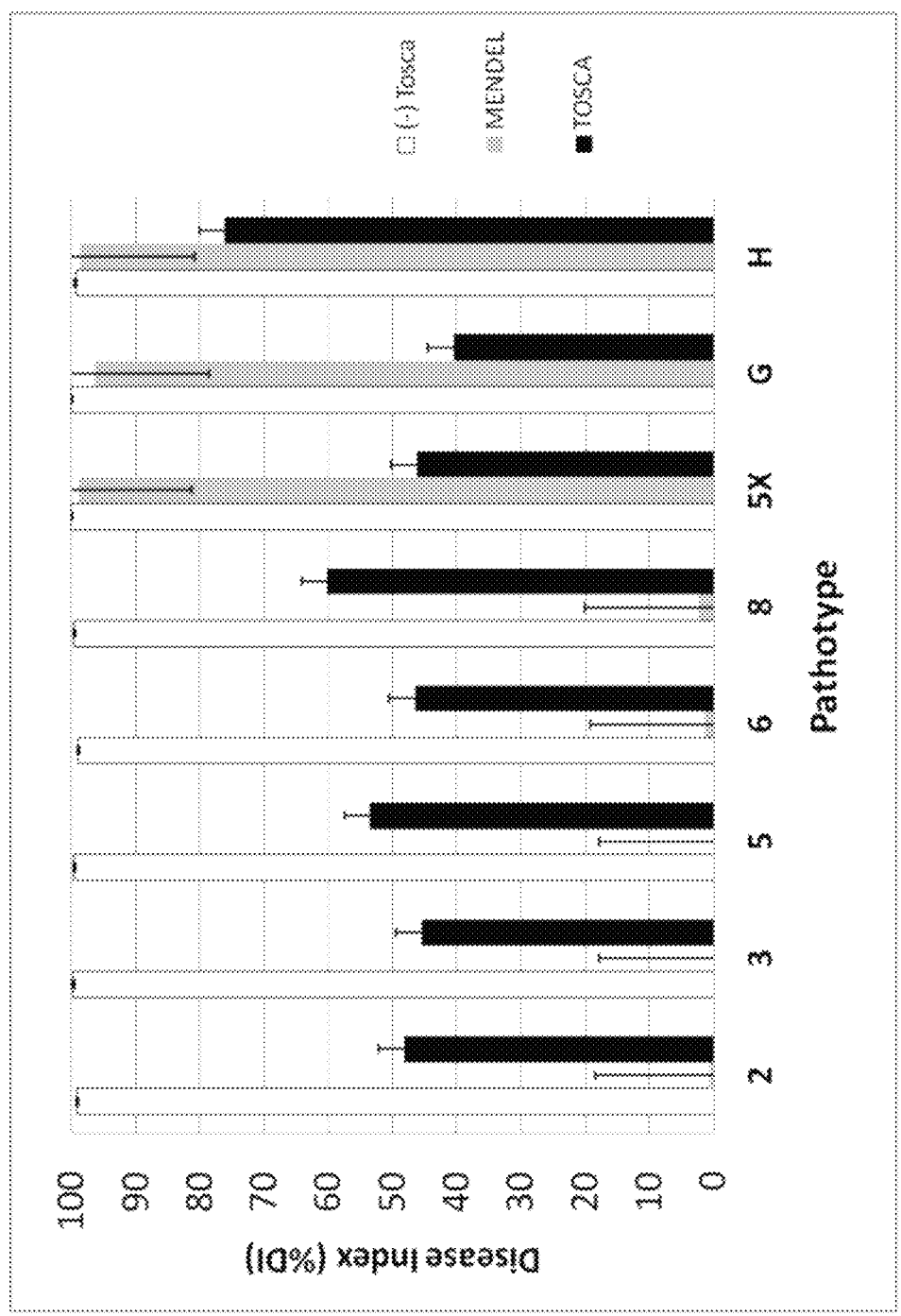
FIG. 2 shows results of a clubroot infection assay showing intermediate resistance provided by canola varieties Tosca and Mendel against clubroot pathotypes 2, 3, 5, 6, 8, 5X, and G.

After six weeks, the roots of each plant are washed with tap water and scored for clubroot symptom development (disease rating) on a 0 to 3 scale as described in Table 1. The disease index is then calculated as described in Example 1. Results are described in FIG. 2. The susceptible check ((-)Tosca) exhibits DIs in the range of 98.9%-100% in all eight inoculations, indicating that the inoculations are successful and that the inoculum is viable. The Tosca-containing lines show intermediate resistance to clubroot pathotypes 2, 3, 5, 6, 8, 5X, and G and is susceptible to pathotype H Example 5. The Clubroot QTL Present in Tosca is Effective Against *P. brassicae* Pathotype 5x

*Brassica napus* plants containing the Tosca-derived Clubroot QTL are inoculated with *P. brassicae* pathotype 5x. Disease ratings are assessed and disease indexes (DIs) are calculated as described in Example 1 and compared to a susceptible check. Plants are rated as either highly resistant (DI<10), resistant (DI between 10 and 20), or moderately-resistant (DI between 20 and 40). All nine lines comprising the Tosca-derived QTL are rated as at least moderately-resistant to clubroot pathotype 5x compared to the susceptible check. (Table 7)

TABLE 7

The clubroot QTL present in Tosca confers at least moderate resistance against *P. brassicae* pathotype 5x.

| Resistance source | Total # of plants | Number of plants rated in each category | | | | DI (%) |
|---|---|---|---|---|---|---|
| | | 0 | 1 | 2 | 3 | |
| Susceptible check | 48 | 0 | 0 | 1 | 47 | 99.3 |
| Tosca 1 | 48 | 28 | 13 | 6 | 1 | 19.4 |
| Tosca 2 | 48 | 23 | 8 | 6 | 11 | 36.8 |
| Tosca 3 | 48 | 41 | 5 | 2 | 0 | 6.3 |
| Tosca 4 | 48 | 43 | 3 | 2 | 0 | 4.9 |
| Tosca 5 | 47 | 38 | 7 | 2 | 0 | 7.8 |
| Tosca 6 | 48 | 35 | 11 | 2 | 0 | 10.4 |
| Tosca 7 | 47 | 37 | 8 | 1 | 1 | 9.2 |

TABLE 7-continued

The clubroot QTL present in Tosca confers at least moderate resistance against *P. brassicae* pathotype 5x.

| Resistance source | Total # of plants | Number of plants rated in each category | | | | DI (%) |
|---|---|---|---|---|---|---|
| | | 0 | 1 | 2 | 3 | |
| Tosca 8 | 48 | 35 | 10 | 3 | 0 | 11.1 |
| Tosca 9 | 48 | 33 | 13 | 2 | 0 | 11.8 |

Example 6. Evaluating Efficacy of the Clubroot QTL from Mendel

The clubroot QTL present in Mendel is analyzed for its resistance efficacy. A doubled haploid progeny population is developed from a cross between MB71780 and *Caiman/Mendel*. Plants are genotyped using markers associated with the Mendel clubroot QTL (Table 4). Plants are grouped as "positive" if they carry the same genotype as Mendel within the QTL interval and "negative" if they carry the same genotype as MB71780 within the QTL interval. The plants are also phenotyped for their resistance to clubroot based on the 0-3 rating as illustrated in Example 1. The phenotyping data are shown is Table 8. The efficacy of the QTL is evaluated based on differences of clubroot disease rating between the positive group and negative group.

A significant difference is observed for the disease rating between the positive and negative groups (p-value shown in Table 8). Lines carrying favorable alleles (resistant alleles) from Mendel provide a reduction of 1.76 points based on the 0-3 phenotype rating (described in Example 1) compared to lines carrying the unfavorable alleles (susceptible alleles) from MB71780. This observation indicates that the QTL present in Mendel can be used to reduce the disease rating by 1.76 points if the QTL is introgressed into lines susceptible to clubroot.

TABLE 8

Efficacy for the Mendel clubroot QTL based on genotype of markers identified as associated with the resistance.

| Disease Rating of Positive Group | Disease Rating of Negative Group | Efficacy | P-value |
|---|---|---|---|
| 0.76 | 2.52 | 1.76 | 6.94182E−20 |

Example 7: Introgression of the Clubroot QTL Present in Tosca into Additional Canola Varieties Experimental hybrids are created using five different male lines containing the Tosca-derived clubroot QTL. Each male line is paired with multiple female lines to create the hybrids, and then all of the hybrids are planted in a clubroot disease nursery to evaluate their resistance level. For each hybrid, 30 individual plants from a plot are evaluated using the method described in Example 1. Hybrids derived from the five male lines all display DI (disease index) scores less than 20% compared to the susceptible check, which exhibits a DI of almost 70% (Table 9).

TABLE 9

Efficacy of Tosca-derived clubroot QTL introgressed into different hybrid backgrounds.

|  | Median DI (%) |
| --- | --- |
| Male parent 1 | 18.8 |
| Male parent 2 | 7.0 |
| Male parent 3 | 2.0 |
| Male parent 4 | 11.7 |
| Male parent 5 | 5.2 |
| Susceptible check | 69.5 |

Additional canola lines are also developed to carry clubroot resistance. A canola plant comprising the Tosca-derived clubroot QTL is crossed with an elite canola line comprising a desirable trait (e.g., improved yield under drought, cold, heat stress conditions) but susceptible to clubroot. $F_1$ progeny plants from this cross are assayed for one or more SNP markers exemplified in Table 3 to select for the clubroot QTL present in Tosca. A selected $F_1$ progeny plant is then backcrossed with the parent elite canola line comparing the desirable trait (recurrent parent). Plants from the BC1 generation are also genotyped using SNP markers exemplified in Table 3 to select for the Tosca-derived clubroot QTL. After multiple rounds of backcrossing (e.g., 5-7 generations), a new elite canola line (which can include a hybrid line) is obtained comparing both clubroot resistance and the desirable trait in the recurrent parent elite line.

Using the above introgression and marker-assisted selection strategy, the pyramiding or stacking of multiple clubroot resistance QTLs can be achieved. Elite canola plants can be made comparing both the Tosca-derived clubroot QTL and another clubroot resistance QTL from a different source with overlapping or complementary pathotype specificity. For example, clubroot resistance QTLs from Tosca and Mendel can be stacked into a single canola variety using markers disclosed herein (for example those listed in Tables 3 and 4). The stacking of resistance QTLs provides clubroot resistance to a broader range of *P. brassicae* pathotypes or multiple modes of action against certain pathotypes which can reduce the risk of resistance being overcome.

As various modifications could be made in the constructions and methods herein described and illustrated without departing from the scope of the disclosure, it is intended that all matter contained in the foregoing description or shown in the accompanying drawings shall be interpreted as illustrative rather than limiting. The breadth and scope of the present disclosure should not be limited by any of the above-described exemplary embodiments, but should be defined only in accordance with the following claims appended hereto and their equivalents. All patent and non-patent documents cited in this specification are incorporated herein by reference in their entireties.

What is claimed is:

1. A method for producing a clubroot-resistant canola plant, said method comprising:
   a) crossing a first clubroot-resistant canola plant comprising at least one clubroot resistance Quantitative Trait Locus (QTL) linked to a polymorphic marker selected from the group consisting of SEQ ID NOs: 1 to 7 with a second canola plant to produce a population of canola plants;
   b) detecting in said population of canola plants a marker linked within 10 cM to said polymorphic marker selected from the group consisting of SEQ ID NOs: 1 to 7; and
   c) selecting a clubroot-resistant canola plant comprising said at least one clubroot resistance QTL from said population;
   wherein said clubroot resistance QTL is linked to at least one polymorphic marker selected from the grouping consisting of:
      a G nucleotide at position 61 of SEQ ID NO:1;
      a C nucleotide at position 61 of SEQ ID NO:2;
      an A nucleotide at position 61 of SEQ ID NO:3;
      a G nucleotide at position 61 of SEQ ID NO:4;
      a G nucleotide at position 150 of SEQ ID NO:5;
      a G nucleotide at position 61 of SEQ ID NO:6; and
      an A nucleotide at position 61 of SEQ ID NO:7.

2. The method of claim 1, wherein said marker is linked within 5 cM of said polymorphic marker selected from the group consisting of SEQ ID NOs: 1 to 7.

3. The method of claim 1, wherein said selected canola plant further comprises at least one clubroot resistance QTL located in a chromosomal segment flanked by SEQ ID NOs: 9 and 12.

4. The method of claim 1, wherein said step (b) comprises genotyping said population of canola plants via a marker detection assay to determine said marker.

5. The method of claim 1, wherein said step (b) comprises detecting a haplotype.

6. The method of claim 5, wherein said haplotype comprises resistance alleles of any two of marker loci SEQ ID NOs: 1 to 7.

7. The method of claim 1, wherein said selected canola plant is a *Brassica napus* plant or a *Brassica rapa* plant.

8. The method of claim 1, wherein said selected canola plant is from a spring canola variety.

9. The method of claim 1, wherein said selected canola plant is highly resistant, resistant or at least moderately resistant to at least one *P. brassicae* pathotype selected from the group consisting of pathotypes 2, 3, 5, 5x, 6, 8, and G.

10. The method of claim 1, further comprising producing a population of progeny from said selected canola plant.

11. The method of claim 1, wherein said selected canola plant further comprises a second clubroot resistance locus selected from the group consisting of Crr1, Crr2, Crr3, Crr4, CRa, CRb, CRc, and CRk.

12. The method of claim 5, wherein said haplotype comprises resistance alleles of SEQ ID NOs: 1 and 2.

13. The method of claim 5, wherein said haplotype comprises resistance alleles of SEQ ID NOs: 1 and 3.

14. The method of claim 5, wherein said haplotype comprises resistance alleles of SEQ ID NOs: 1 and 4.

15. The method of claim 5, wherein said haplotype comprises resistance alleles of SEQ ID NOs: 1 and 5.

16. The method of claim 5, wherein said haplotype comprises resistance alleles of SEQ ID NOs: 1 and 6.

17. The method of claim 5, wherein said haplotype comprises resistance alleles of SEQ ID NOs: 1 and 7.

18. The method of claim 1, wherein said marker is linked within 4 cM to a sequence selected from the group consisting of SEQ ID NOs: 1 to 7.

19. The method of claim 1, wherein said marker is linked within 1 cM to a sequence selected from the group consisting of SEQ ID NOs: 1 to 7.

20. The method of claim 1, wherein said marker is a sequence selected from the group consisting of SEQ ID NOs: 1 to 7.

\* \* \* \* \*